(12) United States Patent
Gibbons et al.

(10) Patent No.: US 11,883,173 B2
(45) Date of Patent: *Jan. 30, 2024

(54) ROADSIDE IMPAIRMENT SENSOR

(71) Applicant: Battelle Memorial Institute, Columbus, OH (US)

(72) Inventors: Scott M. Gibbons, Canal Winchester, OH (US); Aaron J. Frank, Dublin, OH (US); Matthew Kromer, Columbus, OH (US); Bohdan Paselsky, Westerville, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/871,679

(22) Filed: Jul. 22, 2022

(65) Prior Publication Data
US 2023/0018157 A1 Jan. 19, 2023

Related U.S. Application Data

(63) Continuation of application No. 16/655,849, filed on Oct. 17, 2019, now Pat. No. 11,426,107.

(60) Provisional application No. 62/819,049, filed on Mar. 15, 2019, provisional application No. 62/746,723, filed on Oct. 17, 2018.

(51) Int. Cl.
| | |
|---|---|
| *A61B 5/16* | (2006.01) |
| *G06F 3/01* | (2006.01) |
| *G06T 11/00* | (2006.01) |
| *A61B 5/0205* | (2006.01) |
| *A61B 5/01* | (2006.01) |
| *A61B 5/00* | (2006.01) |
| *A61B 5/11* | (2006.01) |
| *A61B 5/291* | (2021.01) |

(52) U.S. Cl.
CPC .......... *A61B 5/165* (2013.01); *A61B 5/0077* (2013.01); *A61B 5/01* (2013.01); *A61B 5/02055* (2013.01); *A61B 5/1114* (2013.01); *A61B 5/163* (2017.08); *A61B 5/291* (2021.01); *A61B 5/6803* (2013.01); *G06F 3/013* (2013.01); *G06T 11/00* (2013.01); *A61B 2562/0219* (2013.01); *A61B 2562/0271* (2013.01); *A61B 2562/185* (2013.01)

(58) Field of Classification Search
CPC ......... A61B 5/165; A61B 5/0077; A61B 5/01; A61B 5/02055; A61B 5/1114; A61B 5/163; A61B 5/6803; A61B 2562/0219; A61B 2562/0271; A61B 2562/185; A61B 5/4845; A61B 5/72–5/7296; G06F 3/013; G06T 11/00

See application file for complete search history.

(56) References Cited

U.S. PATENT DOCUMENTS

| | | | | |
|---|---|---|---|---|
| 5,692,502 A | * | 12/1997 | Alpert | G16H 10/40 600/300 |
| 11,426,107 B2 | * | 8/2022 | Gibbons | A61B 5/1114 |

* cited by examiner

*Primary Examiner* — Jonathan T Kuo
(74) *Attorney, Agent, or Firm* — Lippes Mathias LLP

(57) ABSTRACT

The present disclosure relates generally to a system and method for detecting or indicating a state of impairment of a test subject or user due to drugs or alcohol, and more particularly to a method, system and application or software program configured to creating a virtual-reality ("VR") environment that implements drug and alcohol impairment tests, and which utilizes eye tracking technology to detect or indicate impairment.

20 Claims, 28 Drawing Sheets

FIG. 8

During the test follow these instructions until told the test is over:
- Sit upright in the chair and keep your hands below your chest.
- Keep your head still.
- Follow the movement of the ball with your eyes only.
- You may have to cross your eyes in some tests to maintain focus.
- Keep looking at the ball until told the test is over.

Waiting to continue

ROADSIDE IMPAIRMENT SENSOR

This application is a continuation of U.S. patent application Ser. No. 16/655,849 filed Oct. 17, 2019, which claims priority to U.S. Provisional Patent Application Ser. No. 62/819,049 filed Mar. 15, 2019, which claims priority to 62/746,723 filed Oct. 17, 2018, the entire disclosures of which are incorporated by reference in their entirety herein.

BACKGROUND

The present disclosure relates generally to a system and method for detecting or indicating a state of impairment of a test subject or user due to use of drugs or alcohol, and more particularly to a method, system and application or software program configured to creating a virtual-reality ("VR") environment that implements drug and alcohol impairment tests, and which utilizes eye tracking technology to detect or indicate impairment.

Impairment can be brought about by or as the result of ingesting or otherwise introducing an intoxicating substance, such as alcohol or a drug. Law enforcement officers commonly engage in the detection of a person's impairment, such as during traffic stops or other situations that may arise during the officers' line of duty.

Law enforcement officers currently have access to devices, such as a breathalyzer, which can detect or indicate impairment due to alcohol. However, there is no accepted or ubiquitous device such as the breathalyzer for marijuana and other non-alcoholic drugs. Accordingly, since law enforcement officers do not currently have access to roadside or otherwise portable impairment detectors, decisions regarding impairment typically rely on the subjective judgement of individual officers.

In addition, often a certified Drug Recognition Expert ("DRE") is required to make a decision on a person's impairment. However, the training, certification, and recertification, required by DREs, can be time consuming and costly.

Thus, there is a need for an easy to use, objective, and highly repeatable test, method, and system to assist law enforcement officers in gathering drug impairment indicators. As a result, officers and other officials or test administrators will be empowered to make on-site decisions without needing a certified DRE. Moreover, training and recertification costs will be reduced, allowing time and resources to be redirected to other areas of need.

BRIEF DESCRIPTION

Disclosed herein are systems and methods for creating a virtual-reality ("VR") environment that implements tests from Standard Field Sobriety Tests ("SFSTs") and other drug and alcohol impairment tests used by police officers in the field. The exemplary systems and method are configured, within the boundaries or constraints of VR hardware, to implement such impairment tests as closely as possible to guidelines established by police officers and other agents such as drug recognition experts ("DREs").

More specifically, the impairment tests implemented by the exemplary systems and methods disclosed herein include, but are not limited to: (a) Horizontal Gaze Nystagmus Test—assesses the ability of a test subject to smoothly track a horizontally moving object and checks for eye stability during the test; (b) Vertical Gaze Nystagmus Test—checks for eye stability as the test subject tracks a vertically moving object; (c) Lack of Convergence Test—checks the ability of the test subject to cross his or her eyes when an object is brought towards the bridge of the subject's nose; (d) Pupil size and response test—measures the subject's pupil size in normal lightning conditions, as well as abnormally dark and bright conditions; and, (e) Modified Romberg Balance Test—tests the subject's ability to follow directions, measure time, and balance.

The exemplary systems and methods implement the presently disclosed impairment tests in a virtual world through use of a VR headset configured to include eye tracking hardware and software. As each test is conducted, the exemplary eye tracking hardware and software is capable of accurately measuring pupil size, pupil position, and eye gaze direction independently for each eye at a high sample rate. In order to make determinations of the test subject's level of impairment, the presently disclosed systems and methods calculate various useful values and offsets from the eye tracking data collected during each time step of the VR simulation. The calculated values and offsets based on the eye tracking data is then output as useful information from which determinations of impairment can made objectively, repeatedly, reliably, and accurately, while eliminating or substantially reducing the subjective nature inherent in previous manual impairment tests performed in the field.

In accordance with one particular embodiment, a system configured to implement one or more tests indicative of impairment due to drugs or alcohol is disclosed. The system includes a VR headset configured to display at least one virtual environment and at least one virtual object in the environment. An eye tracking component is also included, and a processor is in communication with a memory which has instructions to measure a change in one or more features of a test subject's eyes with the eye tracking component. The change in one or more features of the test subject's eyes is induced by a manipulation of the at least one virtual environment or the at least one virtual object displayed by the VR headset.

In additional embodiments, one or more sensors are in communication with the eye tracking component. The one or more sensors include cameras, body tracking sensors, accelerometers G-sensors, gyroscopes, proximity sensors, electrodes for obtaining EEG data, and thermometers and other temperature sensors or non-invasive sensing devices.

In other embodiments, a light blocking device is mounted to the VR headset. In further embodiments, one or more light sources are mounted to the VR headset.

In some embodiments, the memory includes a testing component having instructions to perform the one or more tests indicative of impairment. The testing component outputs parameter values for each of the one or more tests.

In further embodiments, the memory also includes a comparison component having instructions to correlate the parameter values output by the testing component with parameter values associated with predetermined baseline standards of impairment. The predetermined baseline standards of impairment can include parameter values related to one or more of a timestamp, a test state, scene settings, left pupil size, right pupil size, eye gaze to target cast distance, eye gaze to target cast vertical angle, eye gaze to target cast horizontal angle, eye horizontal angle to normal, eye vertical angle to normal, distance between eye focus points, eye position, and eye jitter.

In some other embodiments, the memory further includes a decision component having instructions to predict a level of impairment based on the correlation of the comparison component. Moreover, the memory can also include an output component to output the impairment prediction of the decision component or the correlation of parameter values of the comparison component.

In additional embodiments, a host computer is included which is associated or in communication with the VR headset. The host computer has a display device configured to show a real-time representation of the test subject's eyes. In some embodiments, the real-time representation includes a pair of animated eyes and a visual depiction of tracking by the eye tracking component.

In some further embodiments, one or more peripheral devices are included which are connected in communication with the VR headset. The one or more peripheral devices are configured to supplement data generated by the eye tracking component.

In some embodiments, the manipulation of the at least one virtual environment includes a change in brightness, contrast, or color of a scene in the virtual environment. In other embodiments, the manipulation of the at least one virtual object includes a change in brightness, contrast, color, direction, or location of the virtual object. In further embodiments, the manipulation of the at least one virtual object includes random movement, discrete increasing angular movement, smooth movement, or jittery movement of the virtual object.

In accordance with another particular embodiment, a method of indicating impairment due to drugs or alcohol is disclosed. The method includes displaying at least one virtual environment and at least one virtual object in the environment with a VR headset. The VR headset includes an eye tracking component and a processor in communication with a memory, and the memory includes instructions for measuring a change in one or more features of a test subject's eyes with the eye tracking component. The method further includes manipulating the at least one virtual environment or the at least one virtual object displayed by the VR headset; measuring parameter values representative of the change in one or more features of the test subject's eyes after manipulating the virtual environment or the virtual object; and correlating the measured parameter values with predetermined baseline standards of impairment. In addition, a level of impairment based on the correlation with the predetermined baseline standards of impairment can be predicted and output. Further, the correlation with the predetermined baseline standards of impairment can also be output.

In some embodiments, the measuring of parameter values further includes recording at least one of a timestamp, a test state, scene settings, left pupil size, right pupil size, eye gaze to target cast distance, eye gaze to target cast vertical angle, eye gaze to target cast horizontal angle, eye horizontal angle to normal, eye vertical angle to normal, distance between eye focus points, eye position, and eye jitter.

In other embodiments, the manipulating of the at least one virtual object includes changing a brightness, contrast, color, direction, location, or movement of the virtual object.

In further embodiments, the manipulating of the at least one virtual environment comprises changing a brightness, contrast, or color of a scene in the virtual environment.

In accordance with an additional particular embodiment, a method of operating a VR headset to indicate impairment due to drugs or alcohol is disclosed. The method includes: initiating one or more software components configured to perform one or more tests with the VR headset which indicate impairment due to drugs or alcohol; running the selected test according to instructions provided by the one or more software components; activating an eye tracking hardware component to begin recording raw eye tracking data and conditions of at least one virtual tracking object and at least one virtual environment generated by the VR headset; and saving and outputting data generated after running the selected test.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 8 is a screenshot of an instructions screen of the VR headset showing a virtual scene which may be presented to a test subject undergoing an impairment test in accordance with the present disclosure;

DETAILED DESCRIPTION

Figure 1:
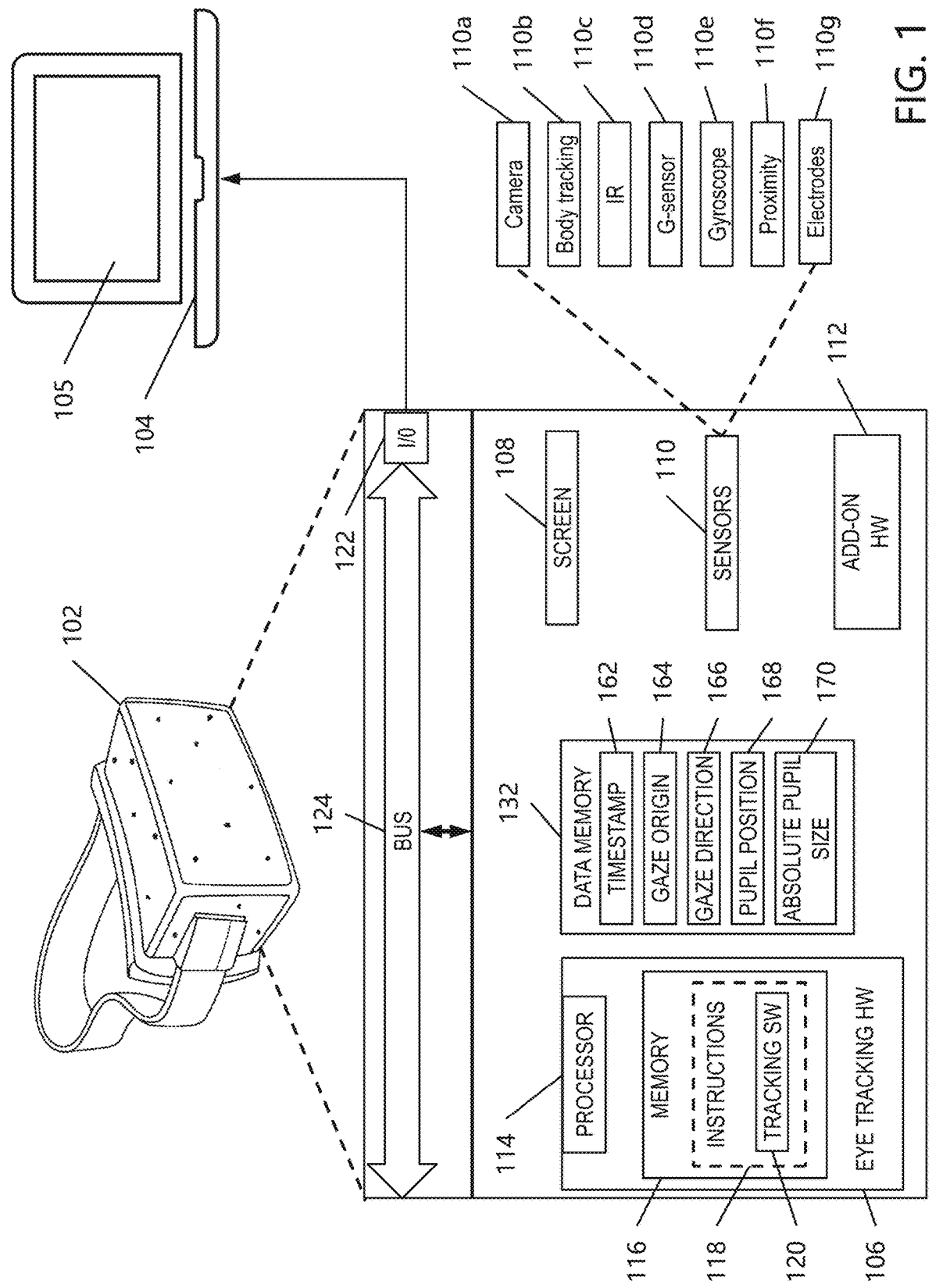
FIG. 1 is a block diagram illustrating a system for performing an impairment test which includes a virtual-reality ("VR") headset and an associated host computer in accordance with one embodiment of the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the terms "comprise(s)," "include(s)," "having," "has," "can," "contain(s)," and variants thereof, as used herein, are intended to be open-ended transitional phrases, terms, or words that require the presence of the named components/ingredients/steps and permit the presence of other components/ingredients/steps. However, such description should be construed as also describing systems or devices or compositions or processes as "consisting of" and "consisting essentially of" the enumerated components/ingredients/steps, which allows the presence of only the named components/ingredients/steps, along with any unavoidable impurities that might result therefrom, and excludes other components/ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number.

The following examples are provided to illustrate the methods, processes, systems, and properties of the present disclosure. The examples are merely illustrative and are not intended to limit the disclosure to the materials, conditions, or process parameters set forth therein.

Figure 2:
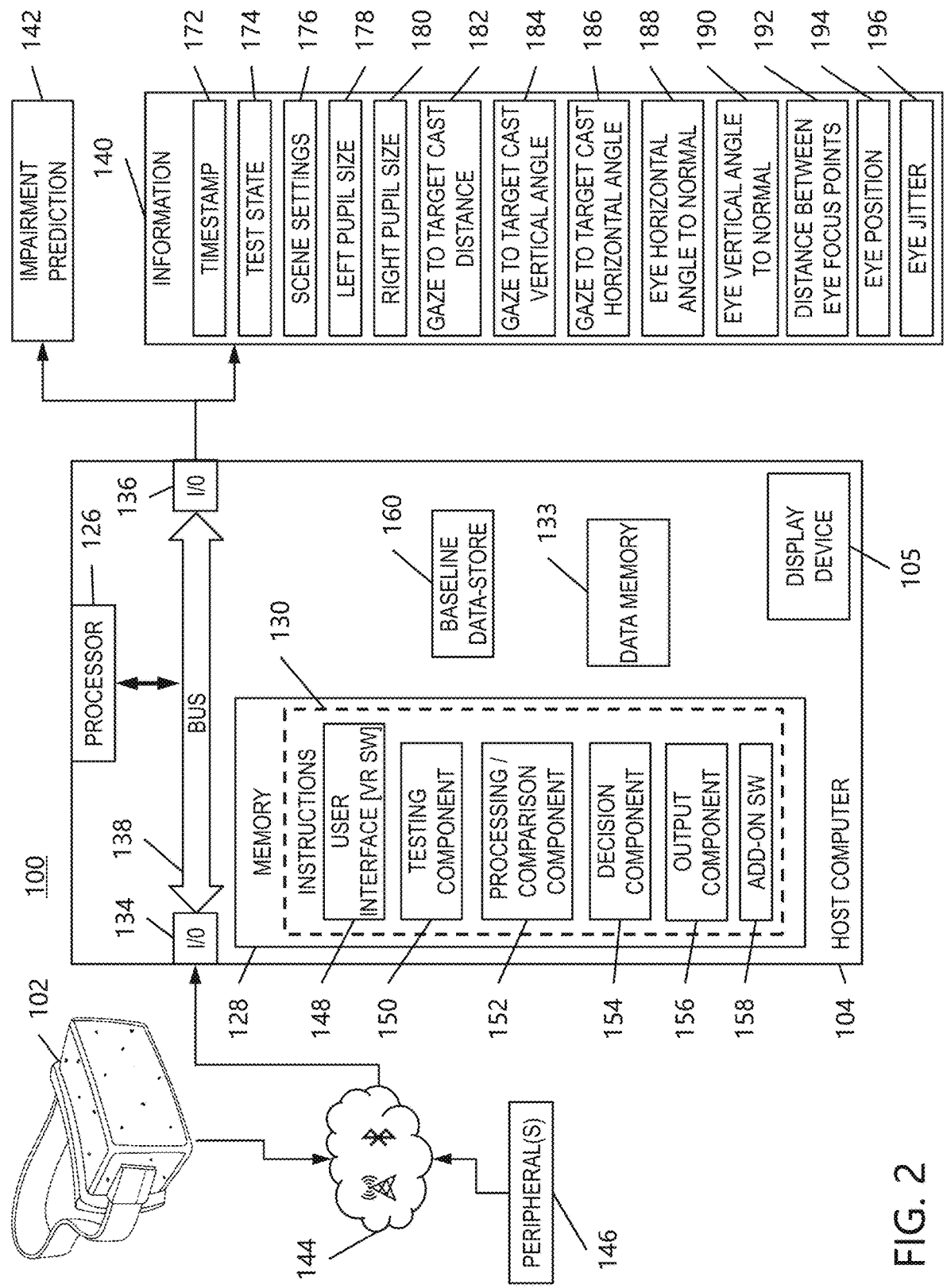
FIG. 2 is a block diagram illustrating additional detail of the system of FIG. 1.

With reference to FIGS. 1-2, block diagrams are illustrated showing a system 100 for performing an impairment test according to an embodiment of the present disclosure. The system 100 generally includes a virtual-reality ("VR") headset unit 102 and an associated host computer 104.

As shown in FIG. 1, the VR headset 102 includes various hardware components, including but not limited to eye tracking hardware 106, a display device such as screen 108, one or more sensors 110, optionally one or more add-on hardware components 112. The eye tracking hardware 106 can be provided as a single chip, such as an application-specific integrated circuit ("ASIC"), which includes a processor 114, local memory 116, and instructions 118 for processing the data generated from the tracking hardware. The instructions 118 may include one or more software components, here illustrated as eye tracking component software 120.

More particularly, eye tracking component software 120 includes computer program code configured to locate, measure, analyze, and extract data from a change in one or more features of a test subject's eyes. The change in one or more features of the test subject's eyes is generally induced by a moving object which the test subject tracks in a virtual scene displayed on the screen 108 of the VR headset 102.

Other changes in the one or more features of the test subject's eyes can be induced, for example, by changing one or more virtual environmental conditions of the virtual scene displayed on the screen 108 of the VR headset 102 (e.g., the brightness of the virtual scene). The local memory 116 stores the instructions 118 to implement the eye tracking software 120, and the instructions are configured to perform at least part of the method illustrated in FIG. 12 (discussed in further detail below). The processor 114, being in communication with the memory 116, executes the instructions 118.

The data generated during processing by the eye tracking hardware 106 and software 120 can be stored in data memory 132, which is separate or integral with local memory 116. In addition, or alternatively, data generated by the eye tracking hardware 106 and software 120 can be output to the host computer 104 for further processing, via input/output (I/O) device 122.

As illustrated in FIG. 1, the raw data stored in memory 132 includes, for example, timestamp 162, eye gaze origin 164, eye gaze direction 166, pupil position 168, and absolute pupil size 170 datasets. Data related to the screen 108, the one or more sensors 110, and the optional one or more add-on hardware components 112 can be similarly stored in data memory 132 and/or output to host computer 104. Hardware components 106, 108, 110, 112, 114, 116, 122, 132 of the VR headset 102 can be communicatively connected by a data/control bus 124.

In some embodiments, the one or more additional sensor components 110 of the VR headset 102 include but are not limited to cameras 110a, body tracking sensors 110b, infrared ("IR") sensors 110c, G-sensors 110d, gyroscopes 110e, proximity sensors 110f, and electrodes 110g for obtaining electroencephalogram (EEG) data. The cameras 110a further optionally include a video recording device which records eye movement during testing. Furthermore, the one or more additional sensor components can include a thermometer or other temperature sensor, along with other non-invasive sensing devices (not shown). The preceding is a non-exhaustive list of exemplary additional sensors and components, and any other desired sensors, devices, or components may be used without departing from the scope of the present disclosure. That is, the skilled artisan will appreciate that other suitable sensors and devices for gathering relevant test subject data can be used in connection with the VR headset 102.

In other embodiments, the add-on hardware 112 can include one or more additional sensors, such as accelerometers (not shown). The add-on hardware 112 can also include one or more additional condition modifiers mounted to the VR headset 102. For example, a light blocking device can be mounted to the VR headset 102 for individual pupil response testing on each eye separately. Similarly, additional illumination devices such as small LED light sources can be mounted to the VR headset 102 for additional testing control on each eye separately.

In other additional embodiments, the eye tracking hardware component 106 can include one or more sensors (not shown), such as eye tracking sensors and IR illuminators. Moreover, the eye tracking hardware component 106 can implement different types of eye tracking techniques, including but not limited to binocular dark pupil tracking.

As shown in FIG. 2, the host computer 104 includes a display device 105, a processor 126, main memory 128, instructions 130, and data memory 133. All the data generated by the eye tracking hardware 106 and the data provided by the screen 108, one or more sensors 110, and one or more optional add-on hardware components 112 of the VR headset 102 and stored in memory 116/132 can be input via input/output (I/O) device 134. The same I/O device 134 may be used to receive information from one or more devices associated with the VR headset 102 and/or host computer 104, such as the illustrated one or more peripheral devices 146.

Figure 12:
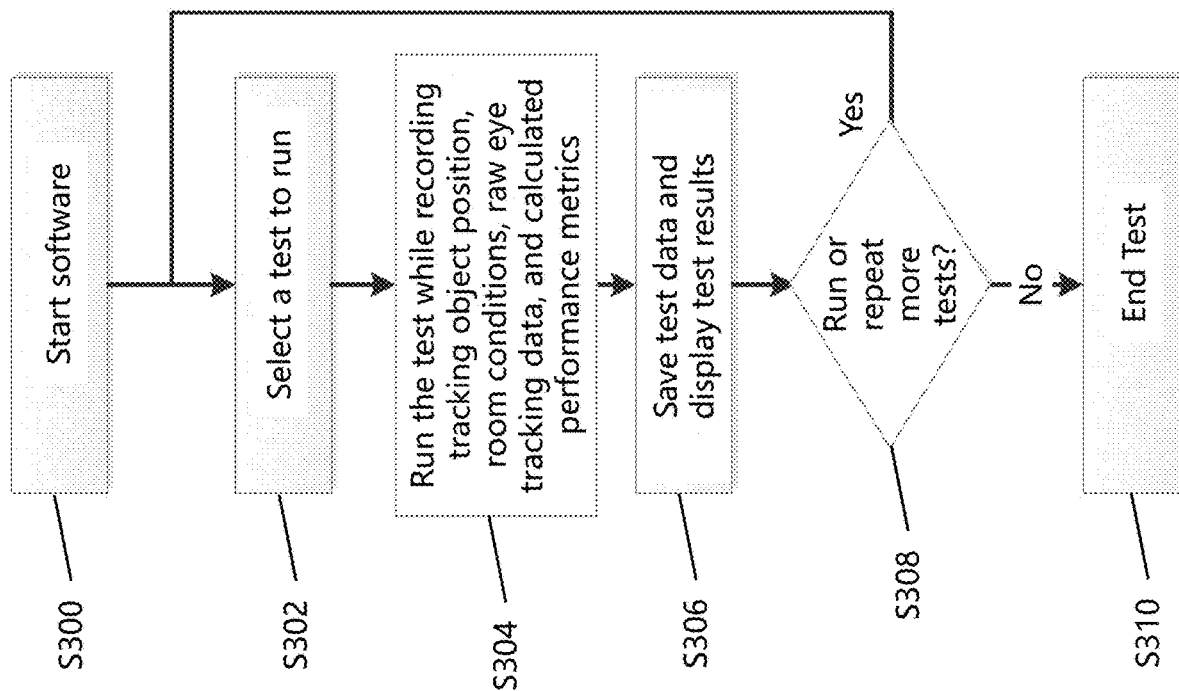
FIG. 12 is flowchart illustrating a method for performing an impairment test which includes a virtual-reality ("VR") headset and an associated host computer in accordance with another embodiment of the present disclosure.

The main memory 128 stores the instructions 130, which are configured to perform at least part of the method illustrated in FIG. 12. The processor 126, being in communication with the memory 128, executes the instructions 130. Data memory 133, which is separate or integral with main memory 128, stores data produced during execution of the instructions 130 by the processor 126. The data stored in memory 128/133 can be output as impairment indicator information 140, via the same I/O device 134 mentioned above or a separate I/O device 136. An impairment prediction 142 (i.e., degree and probability of impairment), based on the impairment indicator information 140, may also be output by the system.

Hardware components 126, 128, 133, 134, and 136 of the host computer 104 can be communicatively connected by a data/control bus 138. The VR headset 102 and the one or more peripheral devices 146 may be communicatively connected with the host computer 102 by a wired or wireless link 144, including but not limited to the Internet, Bluetooth, USB, HDMI, and/or DisplayPort, for example.

The instructions 130 may include several software components, here illustrated as a user interface or VR software 148, an impairment testing component 150, a test processing/comparison component 152, a decision component 154, an output component 156, and any other add-on software 158 associated with the optional add-on hardware 112 included with the VR headset 102. The processor 126 and software components 148-152, 156, and optionally 158 are configured to analyze, extract, calculate, and/or correlate information from the raw data generated by the eye tracking hardware 106 and stored in data memory 132.

More particularly, the user interface 148 includes computer program code to communicate with the user or test administrator via the screen 108 or display device 105 of the host computer 104. For example, once instructed by a user or test administrator, the user interface 148 causes the screen 108 of the VR headset 102 (or host display device 105) to display any number of virtual scenes (such as scene 202 in FIGS. 4-8 and 10 or scene 204 in FIG. 9 discussed in further detail below). Each virtual scene generally includes one or more dynamic component(s) (such as moving target 208 illustrated in FIGS. 9-10) configured to generate a change in one or more features of a subject's eye(s). In addition, when the host computer 104 includes a separate display device 105, real-time test data can be shown on the display device and include, for example, graphical representations of eye position, graphs, charts, etc.

Figure 4:
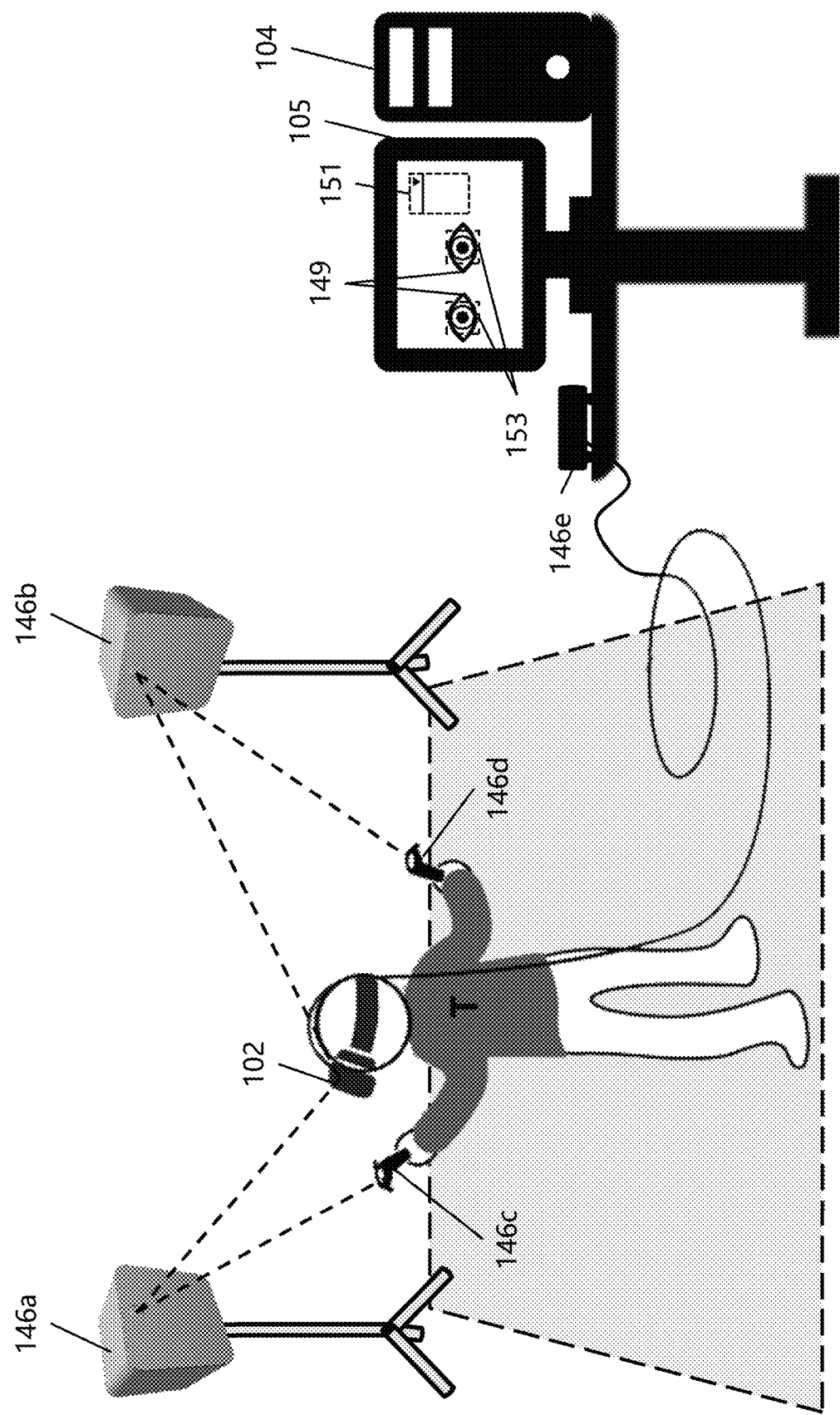
FIG. 4 is an illustration of a test subject undergoing an impairment test operated by the system of the present disclosure.

In some particular examples, as best shown in FIG. 4, the real-time test data displayed on the screen 105 of the host computer 104 is represented by a pair of animated eyes 149 which correspond to the eyes of the test subject. In this regard, the animated eyes 149 presented on the screen 105 show what the test administrator would see if the administrator were able to look directly at the test subject's face. The animated eyes 149 communicate various points of information to the test administrator, such as eyeball position, pupil size, and the open/closed state of the eye. A graphical top down display 151 may also be included on the screen 105 to provide options to display, for example, eyeball location, target ball location, and gaze direction of each eye. The cornea and/or pupil of the animated eyes are each positioned in a square 153 that represents the eye tracking sensor arrays on a normalized coordinate system. However, other visual depictions of the tracking by the eye tracking component could also be used. The display of animated eyes 149 and the information described above on the screen 105 of the host computer 104 displays are useful for the test administrator to verify that proper eye tracking calibration has been performed and that the test subject is following directions.

As discussed above, the eye tracking component 106 of the VR headset 102 is configured to locate, measure, analyze, and extract data from the change in one or more eye features which has/have been induced by the virtual scene displayed on the screen 108 by the user interface 148.

The testing component 150 includes computer program code to store and retrieve from memory components 116, 128, 132, and/or 133, information necessary to perform various impairment tests, including but not limited to lack of convergence ("LOC") test, horizontal and vertical gaze nystagmus tests ("HGN" and "VGN", respectively), pupil dilation test, color sensitivity test, and targeting test. The testing component 150 can further include computer program code to store and retrieve information necessary to perform tests that screen for medical conditions that may affect the results of the various impairment tests (e.g., eye injury, astigmatism, etc.). Similarly, program code for performing tests which rule out conditions could also be included as part of testing component 150. For example, conditions such as optokinetic nystagmus, vestibular nystagmus (resting), etc., may result in a positive impairment indication unless the testing component 150 is configured to test for and rule out these conditions. The information retrieved with the testing component 150 includes but is not limited to: predetermined testing parameters/equations for each impairment test; and, the raw data generated by the eye tracking component 106 and stored in data memory 132 of the VR headset 102.

Moreover, the impairment testing component can optionally be configured to retrieve user data on the subject undergoing the test. User data can be input through the one or more peripheral devices 146 communicatively connected to the VR headset 102 and/or host computer 104, or through a user input device (not shown) associated with the host computer. Once the necessary information is retrieved, the testing component 150 inputs the information into the testing parameters/questions to determine output parameter values for each impairment test performed. The testing component 150 can further include computer program code to update or manage memory components 116 and 128. For example, memory can be updated with customized parameters used by the processing/comparison component 152 and the decision component 154 to calculate the resultant impairment indicating information 140 and impairment prediction 142 of the subject. The parameter values output from the testing component 150 will subsequently be used to determine a test subject's level of impairment and can optionally be stored in data memory 133.

The processing/comparison component 152 includes computer program code to correlate the retrieved testing parameters and associated output values from the testing component 150 with a corresponding baseline standard of impairment/non-impairment and its associated parameter values. More particularly, each of the testing parameters utilized by the testing component 150 are compared with local data-store 160, which contains predetermined or premeasured baseline standards of impairment/non-impairment and their associated parameter values. If a match is found between the testing parameters and the baseline standards, the associated baseline parameter values, or a representation thereof, is/are extracted. The correlations made by the processing/comparison component 152 can optionally be stored in data memory 133. The data-store of baseline standards 160 can also be stored in memory 128.

The processing/comparison component 152 further includes computer program code configured to compare the output values and/or baseline standards with one or more confidence metrics stored in local data-store 160. For example, one confidence metric includes historical data of each individual impairment test result which is accessed by the processing/comparison component 152 to assess the confidence of an indication of impairment. Such historical data could further include drug class identification results with probability or percent matches associated with one or more drug classes. Each of the testing parameters utilized by the testing component 150 are compared with these confidence metrics in the local data-store 160, and if a match is found between the testing parameters/baseline standards and the confidence metrics, the associated confidence metric, or a representation thereof, is/are extracted and are optionally stored in data memory 133.

In addition, or alternatively, the baseline standards, associated baseline parameter values, and associated confidence metrics from data store 160 that have been matched with the testing parameters and associated values output from the testing component 150 are output as impairment indication information 140. That is, the values of each the baseline parameters, confidence metrics, and testing parameters, or representations thereof, are output via output component 156. As illustrated in FIG. 2, the baseline parameters and testing parameters, as well as the values associated therewith, can be related to one or more of a timestamp 172, test state 174, scene settings 176, left pupil size 178, right pupil size 180, eye gaze to target cast distance 182, eye gaze to target cast vertical angle 184, eye gaze to target cast horizontal angle 186, eye horizontal angle to normal 188, eye vertical angle to normal 190, distance between eye focus points 192, eye position 194, and eye jitter 196. These testing parameters are discussed in greater detail below.

Some of the aforementioned testing parameters are directed the state or status of the system 100 itself. For example, the timestamp 172 testing parameter refers to the time that each set of data originates from, measured in seconds, minutes, hours, etc. The test state 174 refers to an integer representing what part of the test is running at the time the sample is taken. For example, the integer "1" may be a test state integer indicating that a first part of the lack of convergence test ("LOC") was running at a timestamp of 30 seconds into the test.

Other testing parameters are directed toward information and data that may be useful for the aforementioned pupil size and response test, along with the color sensitivity test. For example, the scene settings 176 refers to various characteristics of the scene displayed on the screen 108 of the VR headset, including but not limited to scene brightness and scene colors. The brightness in the scene settings 176 is changed for the pupil response test, and specific colors in the scene settings are changed for the color sensitivity test. For example, in the color sensitivity test, VR headset 102 is configured to observe whether the test subject responds to yellow and/or blue colors. In this regard, yellow/blue color vision loss is rare and thus serves as an indicator of impairment. Left pupil size 178 refers to the size of the test subject's left pupil, measured in millimeters by the eye tracking hardware 106 and software 120. Right pupil size 180 refers to the size of the test subject's right pupil, measured in millimeters the eye tracking hardware 106 and software 120.

Some of the other testing parameters are directed toward information and data that may be useful for the aforementioned horizontal and vertical gaze nystagmus tests, as well as the lack of convergence test. For example, the eye gaze to target cast distance 182 refers to the distance between the point where the test subject is looking and the object the test subject is supposed to be looking at, measured in meters by the eye tracking hardware 106 and software 120. The eye gaze to target cast distance 182 is calculated separately for each eye, and the estimated overall point of focus with both eyes is calculated with the eye tracking software 120. The eye gaze to target cast vertical angle 184 refers to the angle between the test subject's gaze and a direct line from their eyes to the tracking object, measured in degrees on the vertical plane by the eye tracking hardware 106 and software 120. The eye gaze to target cast vertical angle 184 is also calculated for each eye and the total gaze. The eye gaze to target cast horizontal angle 186 refers to the angle between the test subject's gaze and a direct line from their eyes to the tracking object, measured in degrees on the horizontal plane by the by the eye tracking hardware 106 and software 120. The eye gaze to target cast horizontal angle 186 is also calculated for each eye and the total gaze. The eye horizontal angle to normal 188 refers to the angle of each eye's gaze relative to the forward direction of the test subject's head, measured in degrees on the horizontal plane by the eye tracking hardware 106 and software 120. The eye vertical angle to normal 190 refers to the angle of each eye's gaze relative to the forward direction of test subject's head, measured in degrees on the vertical plane by the eye tracking hardware 106 and software 120.

Figure 3:
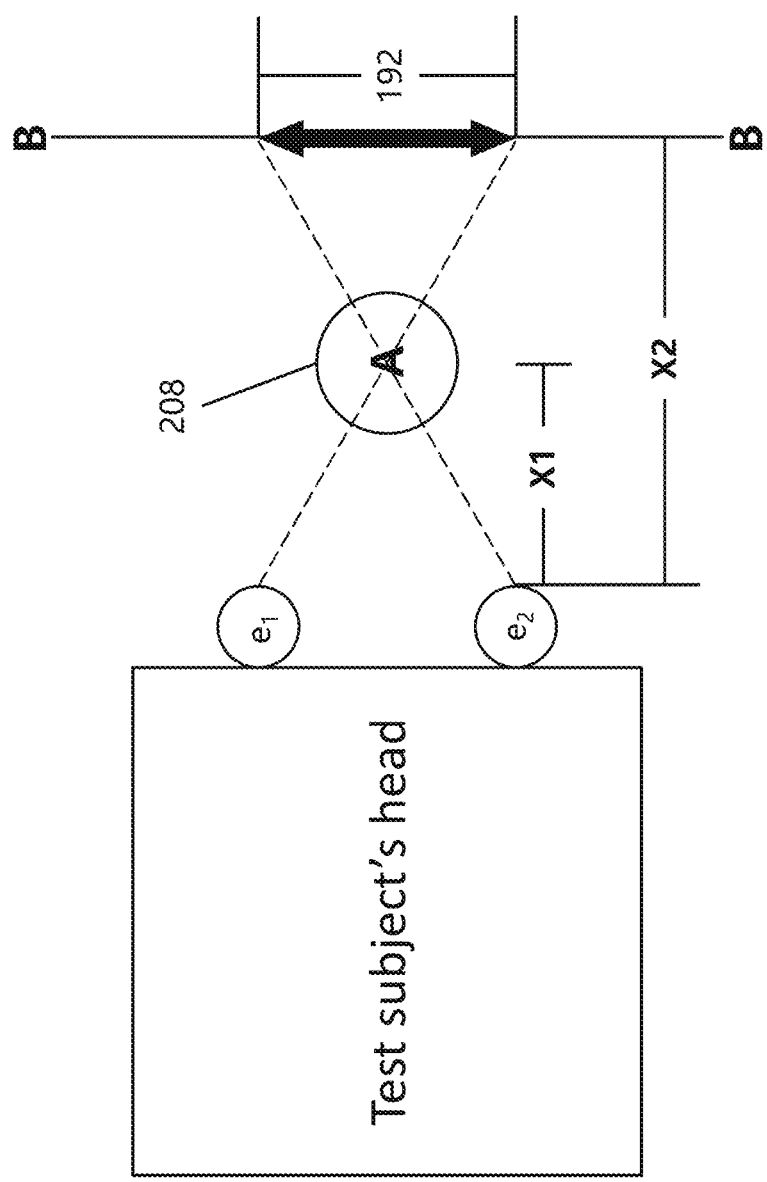
FIG. 3 is an illustration of a testing parameter directed to a distance between eye focus points, the testing parameter being indicative of a test subject's ability to cross his or her.

As illustrated in FIG. 3, the distance between eye focus points 192 testing parameter refers to a numerical indicator, measured by the eye tracking hardware 106 and software 120, of how well the test subject can cross his or her eyes in the lack of convergence test. The distance between eye focus points 192 is measured on reference plane B, relative to the test subject's eyes $e_1$, $e_2$ and focus point A on tracked object 208, where focus point A is located a distance X1 away from the test subject's eyes, and reference plane B is located a distance X2 away from the test subject's eyes that is twice as far as distance X1.

The remaining testing parameters mentioned above are related to eye movement in general, which may be useful for all the aforementioned impairment tests. The eye position 194 refers to the X and Y coordinate position of each of the test subject's pupils within the eye socket, measured by the tracking hardware 106 and software 120. The eye jitter 196 refers to the angle between each test subject's eye's direction and the direction of each eye at the last sample, measured in degrees by the eye tracking hardware 106 and software 120. Eye position 194 and eye jitter 196 information may be particularly useful for the previously mentioned targeting test. The targeting test measures ability to detect the presence of an object that appears in a test subject's field of view and the test subject's ability to focus their gaze on that object. The targeting test is administered by making an object appear at several locations for a set amount of time in the test subject's field of view. In some particular examples, an object appears in eight different locations in the test subject's field of view for about 3 to 5 seconds, where each object location includes a different direction and distance metric. The test subject is instructed to focus their gaze on the target object when detected, and the appropriate eye data is measured and recorded upon detection.

In some embodiments, after the processing/comparison component 152 has made correlations, the optional decision software component 154 is then utilized. The decision software component 154 includes computer program code to predict a level of impairment (that is, predict a probability and degree of impairment of a test subject), based on the correlated parameter values determined by the processing/comparison component 152. That is, for any testing parameter and baseline standard being correlated by the processing/comparison component 152, if the testing parameter output value(s) exceeds one or more thresholds (e.g., value(s) over a period of time, too many high and/or low values, total value too high/too low, etc.) set for the corresponding baseline output value(s), the decision component 154 may output a prediction 142 that the test subject is impaired at an estimated degree. The impairment prediction 142 of the decision component 154 can optionally be stored in data memory 133. In addition, or alternatively, the impairment prediction 142, or a representation thereof, can be output to the test subject or test administrator via the output component 156. The output component 156 can output the impairment prediction 142 alone or together with the correlated baseline standards, associated baseline parameter values, testing parameters, and associated testing parameter values.

In other embodiments, the decision software component 154 is not utilized. That is, the host computer 104 does not make an impairment prediction. In such embodiments, a user or administrator of the VR headset 102 and host computer 104 may prefer to make his/her own impairment prediction based on a review of the impairment indication information 140. In such cases, only the impairment indication information 140 (i.e., the correlated baseline standards, associated baseline parameter values, testing parameters, and associated testing parameter values, or representations thereof) is output via output component 156.

In any event, the output component 156 includes computer program code to output one or both impairment indication information 140 and impairment prediction 142, or a representation thereof. More particularly, information 140 and prediction 142 are output by the output component 156 and to the user interface 148, such that the screen 108 of the VR headset 102 and/or display device 105 of the host computer 104 can display the information to the test subject or test administrator. Moreover, the eye data saved for each test subject in information 140 is saved in at least one memory component 116, 128, 132, or 133 of the VR headset 102 or host computer 104. Generally, the information 140 is saved in an appropriate format which enables the loading and replaying of test data files for any test subject. If desired, the entire test for a test subject can be replayed using the animated eyes 149 shown on the display device 105 of the host computer 104 as described above. In some particular examples, the information 140 can be saved to memory in the XML format.

The host computer 104 can include any number of known user input devices (not shown), such as a keyboard, touch or writable screen, voice or AI assistant, and/or a cursor control device, such as mouse, trackball, or the like, used by a user for inputting additional desired information. Alternatively, such user input devices can be directly connected to the VR headset 102 for inputting the additional information. The computer 104 may include a PC, such as a desktop, a laptop, server computer, cellular telephone, tablet computer, etc., or a combination thereof.

The memory components 116, 128, 132, and 133 of both VR headset 102 and host computer 104 may represent any type of non-transitory computer readable medium such as random-access memory (RAM), read only memory (ROM), magnetic disk or tape, optical disk, flash memory, or holographic memory. In one embodiment, the memory components 116, 128, 132, and 133 comprises a combination of random access memory and read only memory.

In some embodiments, the processors 114 and 126 of the VR headset 102 and host computer 104, respectively, along with associated memory components 116, 132 and/or 128, 133 may be combined in a single chip. In addition, processors 114 and 126 can be variously embodied, such as by a single-core processor, a dual-core processor (or more generally by a multiple-core processor), a digital processor and cooperating math coprocessor, a digital controller, or the like.

Turning now to FIG. 4, an illustration is provided which demonstrates use of the exemplary systems and methods for creating a VR environment to implement impairment tests. Test subject T is illustrated wearing the exemplary VR headset 102 having all the features described above. The VR headset 102 is communicatively connected to the host computer 104, such as through peripheral connection or link device 146. The "virtual world" in which the VR impairment test of the present disclosure is administered to test subject T can be given dimensions through the use of one or more peripheral devices 146a and 146b, which are communicatively connected to VR headset 102 and/or host computer 104. Peripheral devices 146a and 146b illuminate the outlined space in FIG. 4 with IR light. As described in greater detail above, the VR headset 102 can include one or more IR sensors configured to receive the IR light generated by the peripheral devices 146a and 146b, and thereby define the dimensions of the virtual world.

Moreover, one or more handheld peripheral devices 146c and 146d can also be communicatively connected with one or both the VR headset 102 and host computer 104. The one or more handheld peripheral devices 146c and 146d can also include one or more IR sensors configured to receive the IR light generated by the peripheral devices 146a and 146b. In this regard, the eye tracking data generated by the eye tracking hardware of the VR headset 102 can be supplemented with additional data generated, recorded, extracted, analyzed, etc., by the responses of test subject T's hands and arms via handheld peripheral devices 146c and 146d. However, such a configuration is non-limiting.

Figure 5:
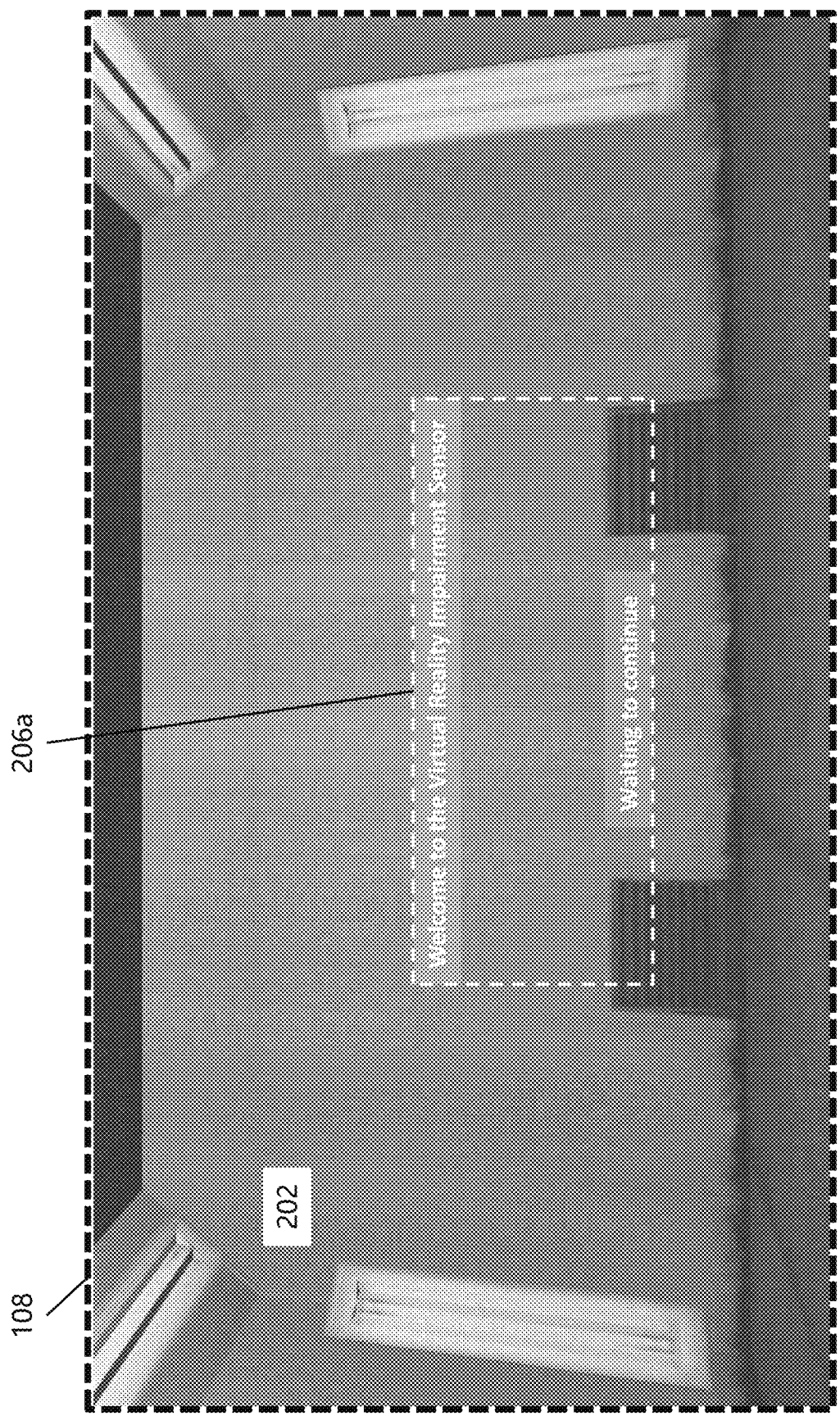
FIG. 5 is a screenshot of a welcome screen of the VR headset showing a virtual scene which may be presented to a test subject undergoing an impairment test in accordance with the present disclosure.

Referring now to FIGS. 4-10, one or more virtual scenes 202, 204 are illustrated as would be displayed: (a) to a test subject undergoing the one or more impairment tests of the present disclosure (such as test subject T in FIG. 4); and (b) on the screen 108 of the VR headset 102 described above. In FIG. 5, the screen 108 shows a virtual scene 202 representing an empty room where the subject VR impairment tests will take place. It should be understood that the empty room illustrated in virtual scene 202 is only exemplary, and any desired scene may be replicated in the virtual world on screen 108 without departing from the scope of the present disclosure. The screen 108 and virtual scene 202 illustrated in FIG. 5 are representative of a welcome screen that would be seen by a test subject, as indicated by the test labeled 206a.

Figure 6:
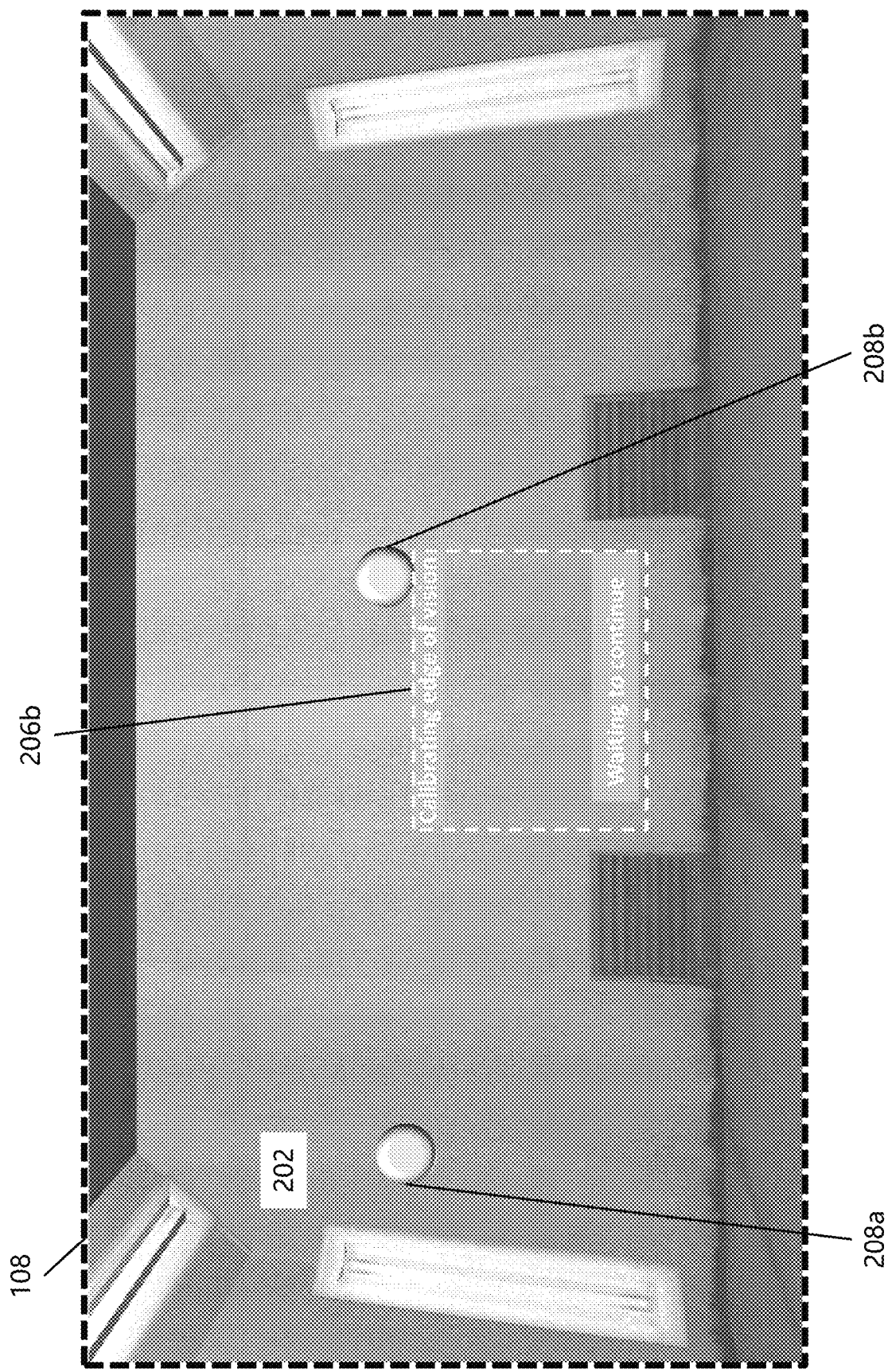
FIG. 6 is a screenshot of a calibration screen of the VR headset showing a virtual scene which may be presented to a test subject undergoing an impairment test in accordance with the present disclosure.

In FIG. 6, the screen 108 shows the same virtual scene 202 as shown in FIG. 5, with the exception that two tracking objects 208a and 208b are now presented. As indicated by the text 206b, the virtual scene 202 illustrated in FIG. 6 is representative of a calibration process for a test subject to ensure that the exemplary VR headset of the present disclosure is properly positioned, with respect to the test subject's field of vision, to obtain data from the eye tracking hardware and software components, as well as any from other connected devices, sensors, etc., that may be communicatively connected to the VR headset or host computer. The two tracking objects 208a and 208b illustrated in FIG. 6 are simple spheres which are configured to move around the screen 108 based on the instructions provided by the eye tracking software.

Figure 7:
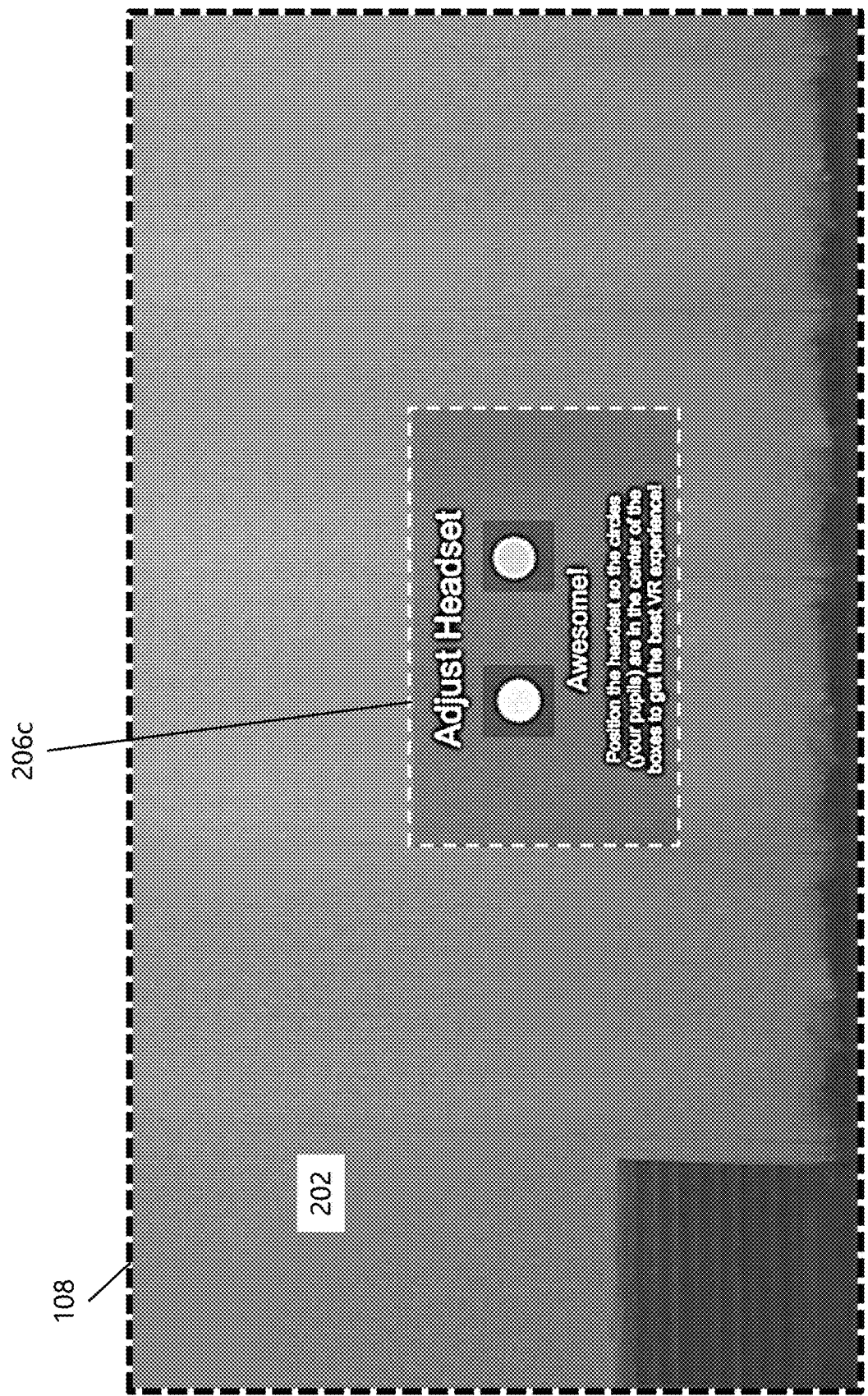
FIG. 7 is a screenshot of an additional calibration screen of the VR headset showing a virtual scene which may be presented to a test subject undergoing an impairment test in accordance with the present disclosure.

In FIG. 7, the screen 106 shows a partially zoomed in view of virtual scene 202 from FIGS. 5 and 6. However, the illustration in FIG. 7 is representative of a calibration process for adjusting the position of the entire VR headset, as indicated by text 206c.

In FIG. 8, the screen 108 shows a similar virtual scene 202 as that of FIGS. 5-7. However, as indicated by the text 206d, the virtual scene 202 illustrated in FIG. 8 is representative of an instruction screen presented to a test subject undergoing the exemplary impairment tests of the present disclosure.

Figure 9:
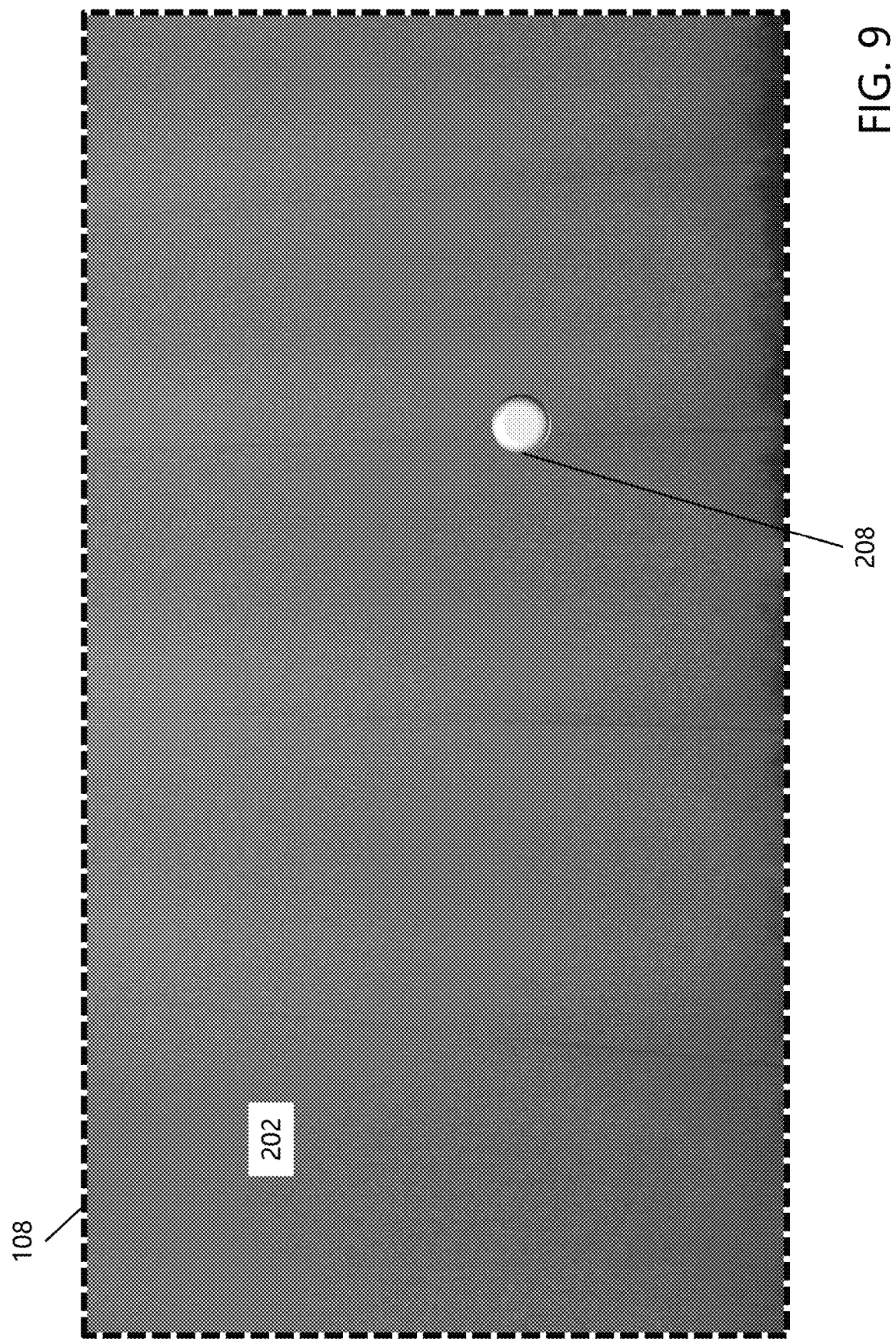
FIG. 9 is a screenshot of an additional eye tracking calibration screen of the VR headset showing a virtual scene which may be presented to a test subject undergoing an impairment test in accordance with the present disclosure.

In FIG. 9, the screen 106 shows another zoomed in view of virtual scene 202 from FIGS. 5, 6 and 8. In accordance with one example, the illustration in FIG. 9 is representative of a calibration process for the tracking of the eye tracking hardware and software components. As illustrated in FIG. 9, one tracking object 208 is presented. The tracking object 208 illustrated in FIG. 9 is a simple sphere which is configured to move around the screen 108 based on the instructions provided by the eye tracking software 120. As another example, the illustration in FIG. 9 is representative of a screen presented to a test subject during eye tracking data generation and collection for the aforementioned targeting test. In this regard, during administration of the targeting test, the tracking object 208 would appear at one of several different locations on screen 108, for about 3 to 5 seconds at each location, so that the test subject's ability to detect and focus on the object can be measured.

Figure 10:
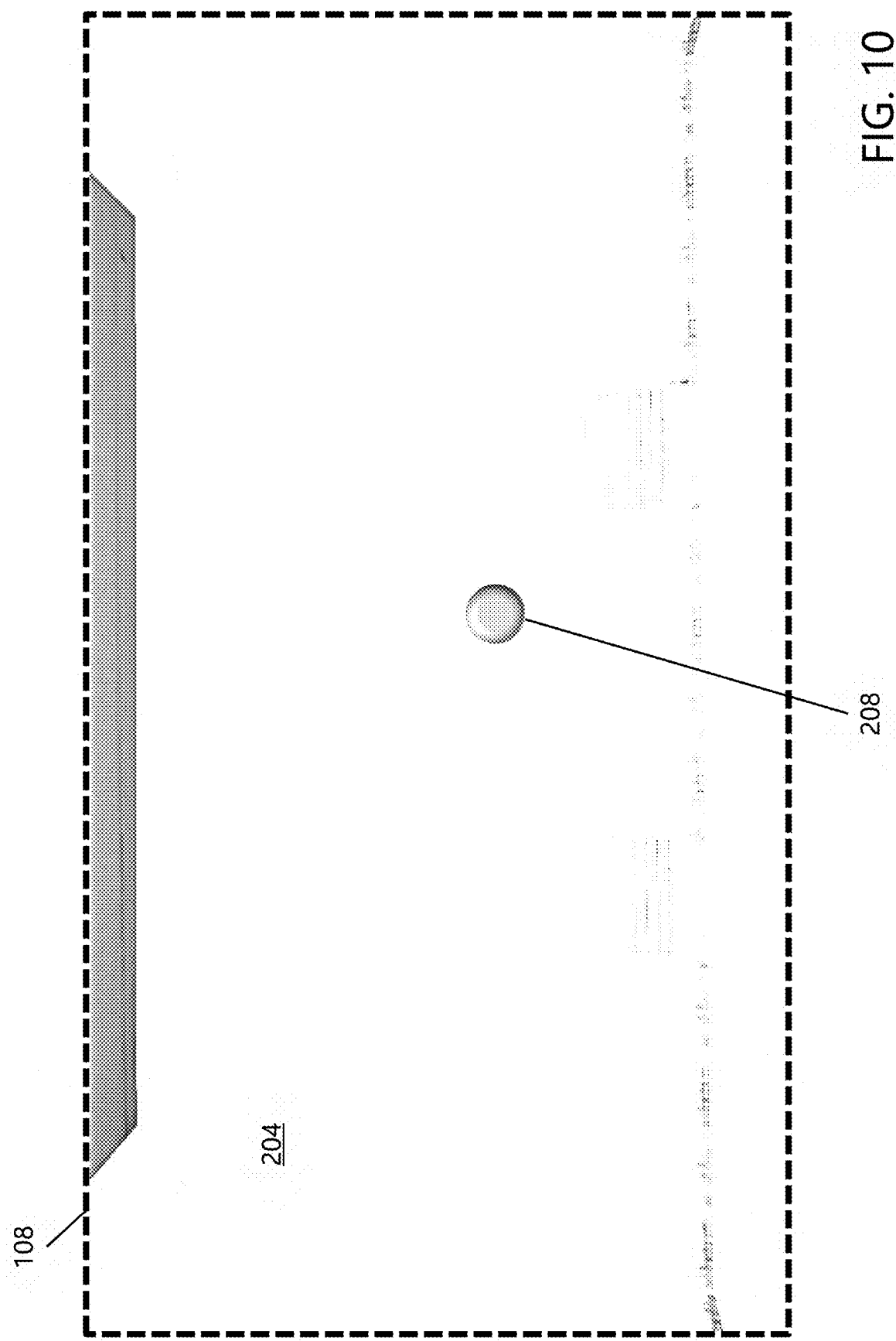
FIG. 10 is a screenshot of a screen of the VR headset showing a virtual scene having an increased brightness and which may be presented to a test subject undergoing an impairment test in accordance with the present disclosure.

In FIG. 10, the screen 108 shows a new virtual scene 204, where the tracking object 208 from FIG. 9 is still present, but one or more virtual environmental conditions have changed. More particularly, FIG. 10 is representative of a screen presented during eye tracking data generation and collection when a brightness of the scene settings 176 is increased for the pupil response test. Such a change in environmental conditions can be presented to a test subject when it is desired to perform a pupil size and response test for impairment, where left pupil size 178 and right pupil size 180 are measured. Another example of changing a virtual environmental condition similar to the scene brightness in FIG. 10 includes changing the color of the tracking object 208 to yellow/blue and measuring the test subject's tracking response. An additional example, referred to as a "random tracking test", involves recording the test subject's eye reactions when the tracking object 208 appears randomly at points in the space of virtual scene 204. In yet another example, the tracking object 208 or other visual stimulus appears at discrete increasing angles from the test subjects instead of smooth movement across the virtual scene 204. Such a test is useful for measuring the angle of onset of gaze nystagmus. In a further example, the contrast of the tracking object 208 or other visual stimulus can be changed. Contrast control is useful to ensure that the VR headset 102 operates correctly for color blind test subjects.

Figure 11:
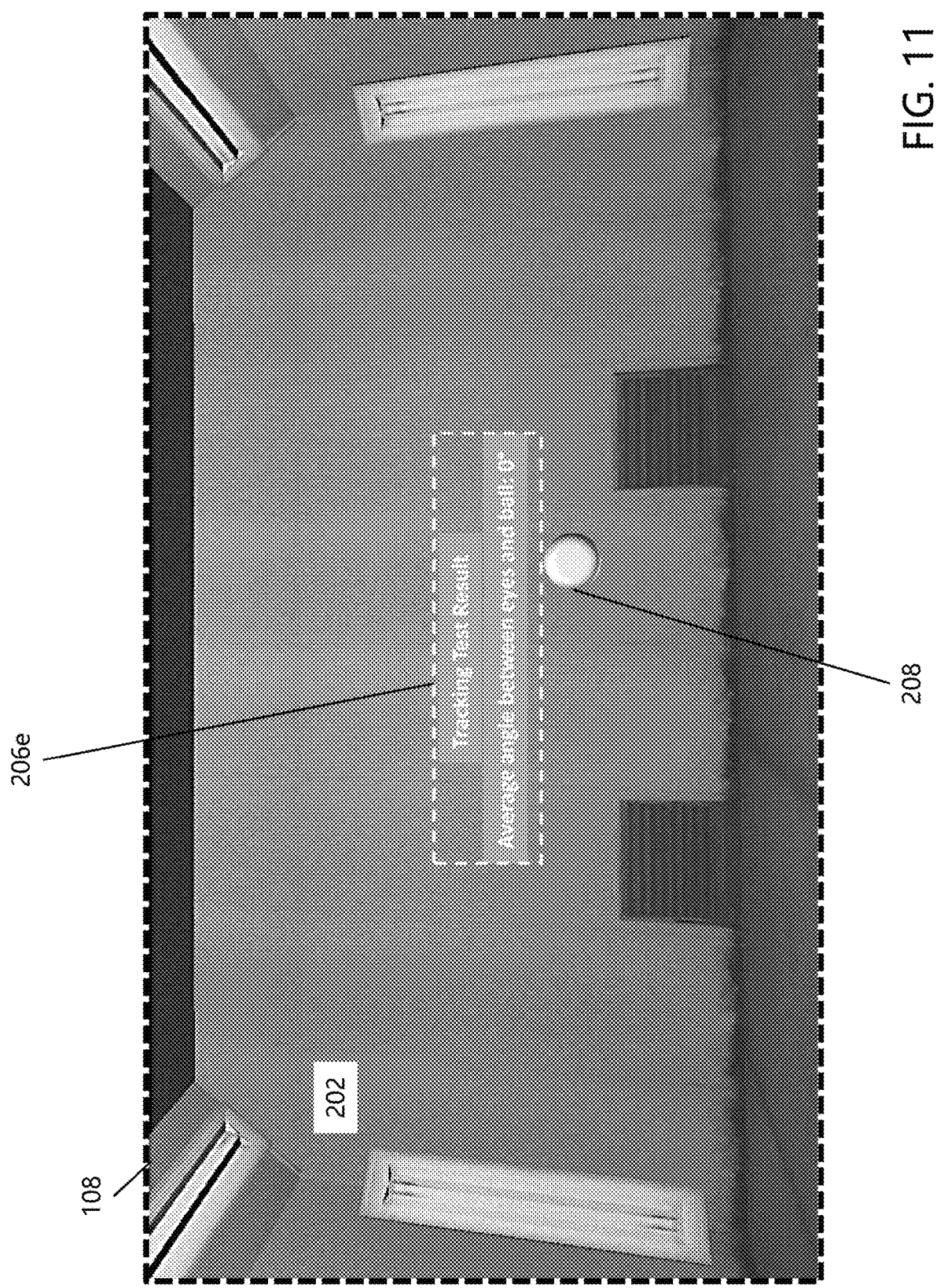
FIG. 11 is a screenshot of a screen of the VR headset showing a virtual scene having and eye tracking test result and which may be presented to a test subject undergoing an impairment test in accordance with the present disclosure.

Finally, in FIG. 11, the screen 108 shows the previous virtual world 202 with the brightness level returned to normal compared with FIG. 10. FIG. 11 also includes the one tracking object 108 configured to move around the screen 108 based on the instructions provided by the eye tracking software 120.

As indicated by text 206e, the virtual scene 202 as illustrated in FIG. 11 is representative of a result or output screen that would be presented to a test subject or test administrator after completion of one of the one or more exemplary VR impairment tests of the present disclosure. More particularly, as indicated by text 206*e*, the FIG. 10 is representative of a result or output screen presented after eye tracking data generation and collection for one or more of the impairment indication information described above, such as eye gaze to target cast vertical angle 184, eye gaze to target cast horizontal angle 186, or eye horizontal angle to normal 188. Such data may be generated and collected during administration of, for example, the horizontal or vertical gaze nystagmus impairment tests discussed above.

Turning now to FIG. 12, a flowchart is illustrated that represents an exemplary method for performing an impairment test according to an embodiment of the present disclosure. The method begins at S300, where the software components described above with respect to the VR headset 102 and host computer 104 are initiated for performing the one or more VR impairments tests. Next, at S302, at least one of the one or more VR impairments tests are selected for administration by a test subject or test administrator using VR headset 102 and host computer 104. At S304, the one or more selected VR impairment tests are run according to the instructions and software components included in the VR headset 102 and host computer 104. In addition, the associated hardware components of VR headset 102 and host computer 104, such as eye tracking hardware 106, are activated to begin recording tracking object position, room conditions, raw eye tracking data, and calculated performance metrics, such as those described in data memory 132. At S306, the method continues with saving test data generated after running the one or more selected VR impairment tests and results thereof are output and displayed to one or both of the test subject and test administrator. At S308, the method determines whether it is necessary to run one or more additional VR impairment tests, and/or repeat the previously selected one or more VR impairment tests. If yes, the method returns to step S302 discussed above. If no, the test(s) end at S310.

Figure 13:
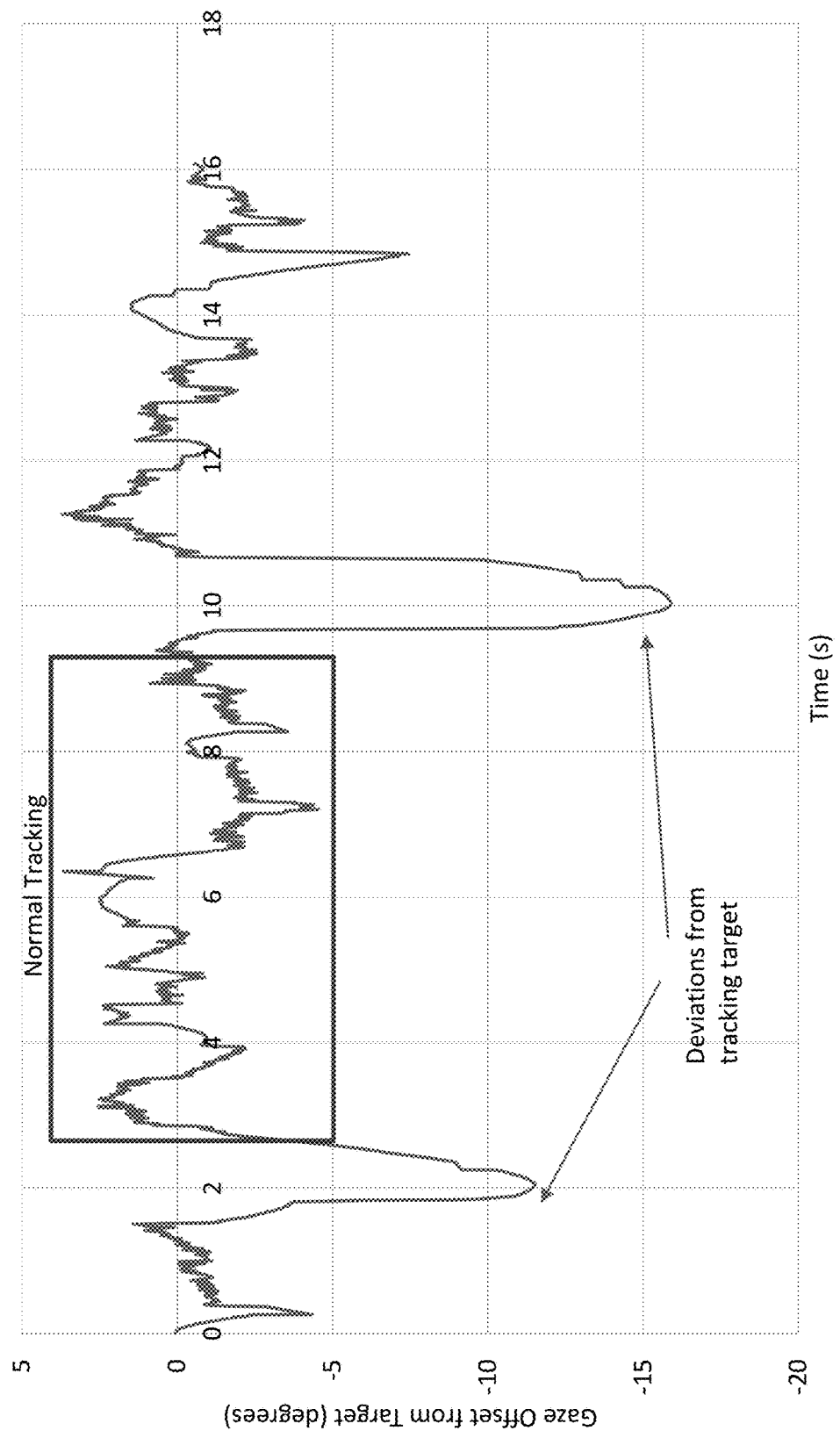
FIG. 13 is an illustration of an exemplary chart which may be output by the system of the present disclosure and which shows the results of a Smooth Pursuit Test for tracking eye movement.

Turning now to FIGS. 13-17, various charts are presented which illustrate some results of representative of the exemplary one or more VR impairment indicator tests discussed above. In FIG. 13, a chart titled "Smooth Pursuit Test" is provided which shows an exemplary eye tracking test having short durations. The Smooth Pursuit Test of FIG. 13 is representative of the type of information output as part of the impairment indication information 140 described above. In particular, FIG. 13 includes values for at least one of the eye gaze to target cast vertical angle 184 or eye gaze to target cast horizontal angle 186 testing parameters, as shown on the Y-axis labeled "Gaze Offset from Target (degrees)". Such data would be generated and collected over the timestamp testing parameter values shown on the X-axis and during administration of, for example, the horizontal or vertical gaze nystagmus impairment tests discussed above. Moreover, the testing parameter labeled as "Deviations from tracking target" are representative of values which may indicate impairment, as these deviations fall well outside the indicated baseline or "Normal Tracking" parameter values.

Figure 14:
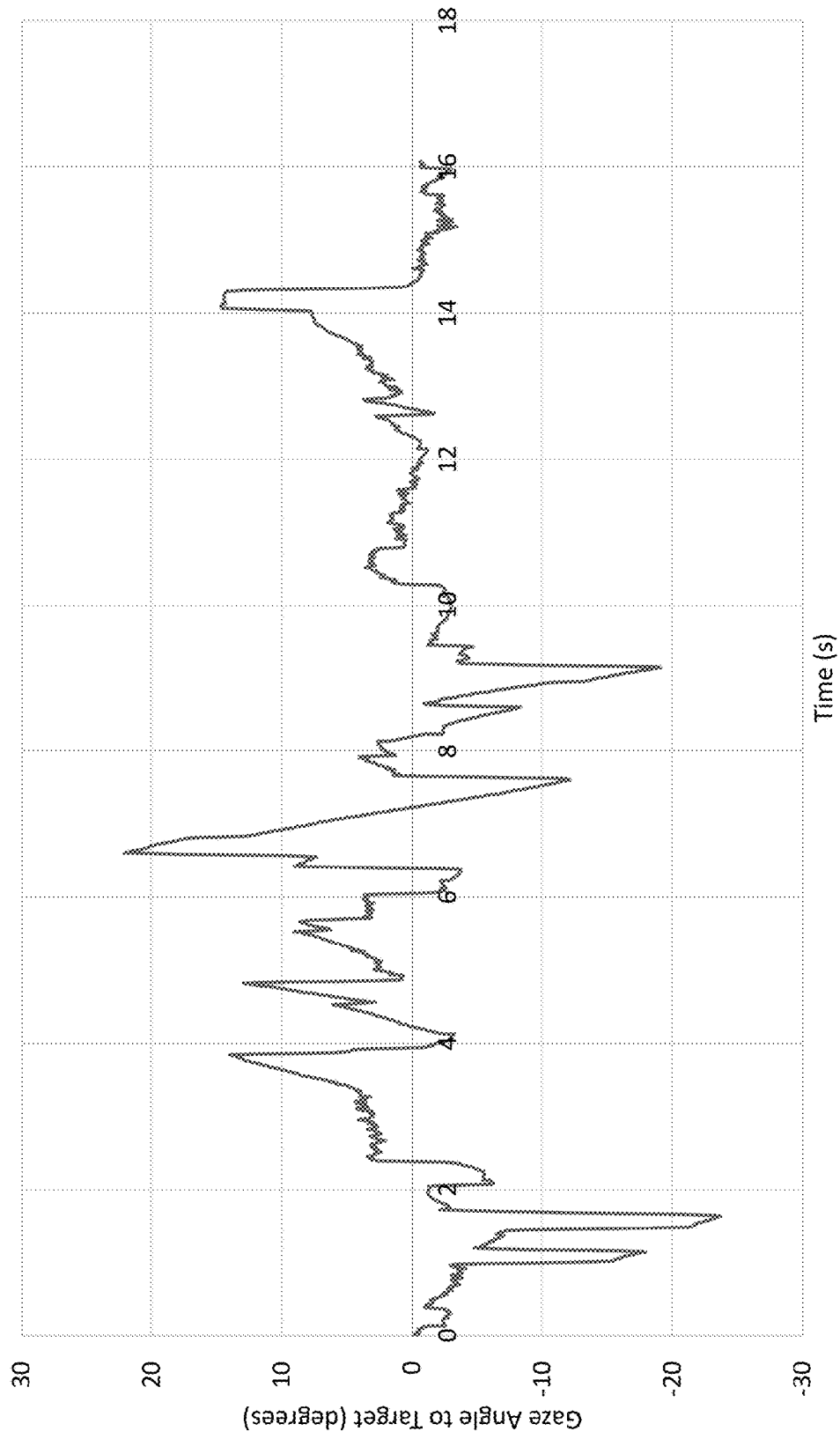
FIG. 14 is an illustration of another exemplary chart which may be output by the system of the present disclosure and which shows the results of a Smooth Pursuit Test for tracking eye movement where the test subject exhibits jittery eye movement.

In FIG. 14, another chart titled "Smooth Pursuit Test" is provided which shows an exemplary eye tracking test for a horizontally moving object having jittery motions. The Smooth Pursuit Test of FIG. 14 is again representative of the type of information output as part of the impairment indication information 140 described above. In particular, FIG. 14 includes values for the eye gaze to target cast horizontal angle 186 and eye jitter 196 testing parameters. Such data would be generated and collected over the timestamp testing parameter values shown on the X-axis and during administration of, for example, the horizontal or vertical gaze nystagmus impairment tests discussed above. Moreover, the results illustrated in the chart of FIG. 14 are representative of testing parameter values which may indicate impairment, as the plot line in FIG. 14 is jagged and jittery and an indication of non-impairment would likely result in a smooth line over time (i.e., less deviations on the Y-axis labeled "Gaze Angle to Target (degrees)".

Figure 15:
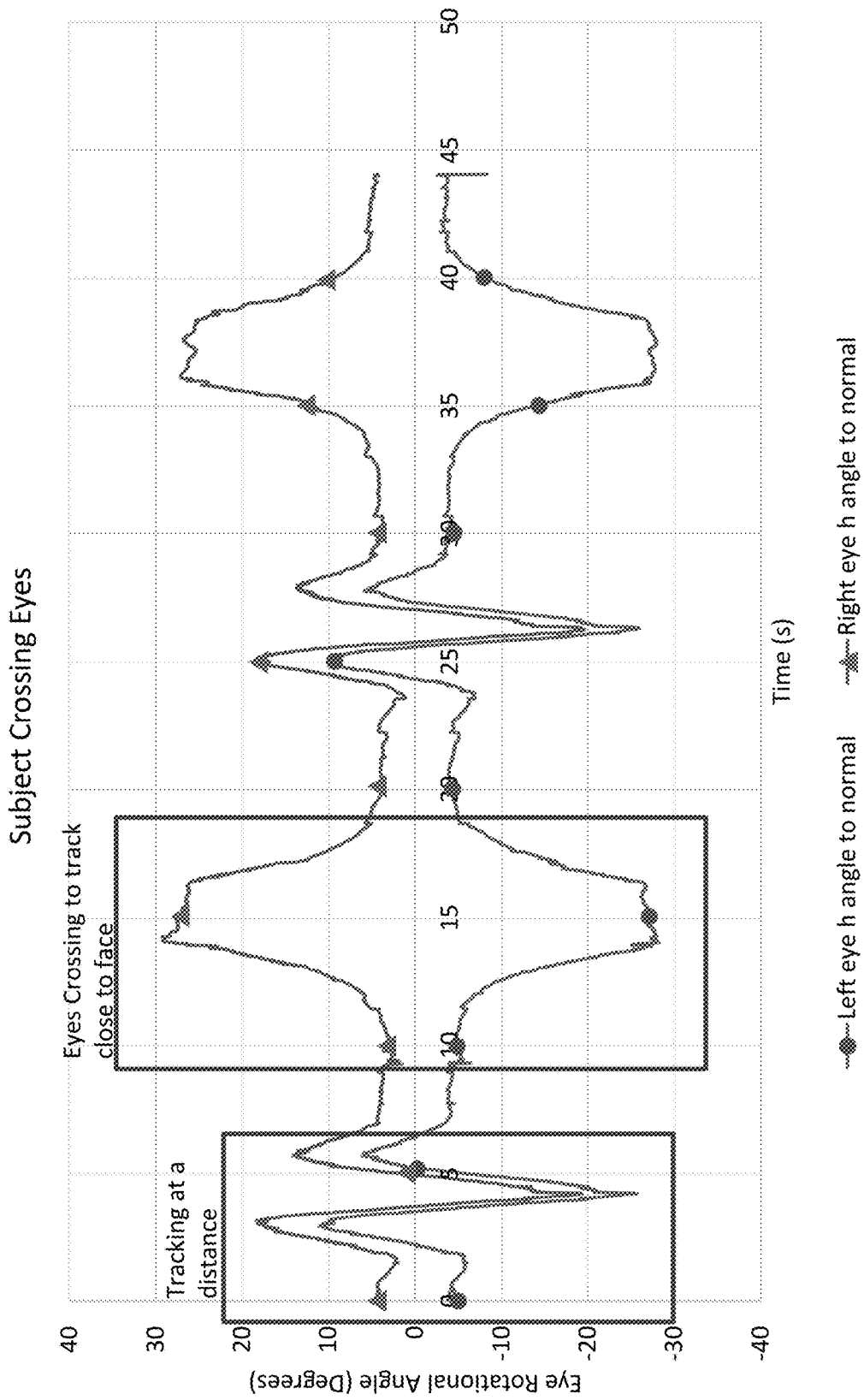
FIG. 15 is an illustration of an additional exemplary chart which may be output by the system of the present disclosure and which shows the results of a Lack of Convergence Test for tracking eye movement where the test subject is likely not impaired.

In FIG. 15, a chart titled "Lack of Convergence Test" is provided which shows an exemplary eye tracking test when the test subject is crossing his or her eyes. The Lack of Convergence Test result in the chart of FIG. 15 is further representative of the type of information output as part of the impairment indication information 140 described above. More particularly, FIG. 15 includes values that would be expected for the eye horizontal angle to normal 188 and eye vertical angle to normal 190 testing parameters, as indicated by the chart key which labels the two data plot lines as "Left eye h angle to normal" and "Right eye h angle to normal", as well as the Y-axis labeled "Eye Rotational Angle (Degrees)". Such data would be generated and collected over the timestamp testing parameter values shown on the X-axis and during administration of the Lack of Convergence Test as described above. Moreover, the testing parameter values, as represented by the data plot lines for each eye in FIG. 15, are representative of values which may indicate non-impairment. This is because the left and right eye angles h to normal run substantially proportional to one another at the data plot lines indicated as "Tracking at a distance", as would be expected in a non-impaired state. This is also because the left and right eye angles h to normal run substantially inversely proportional to one another at the data plot lines indicated as "Eyes crossing to track close to face", as would be expected in a non-impaired state.

Figure 16:
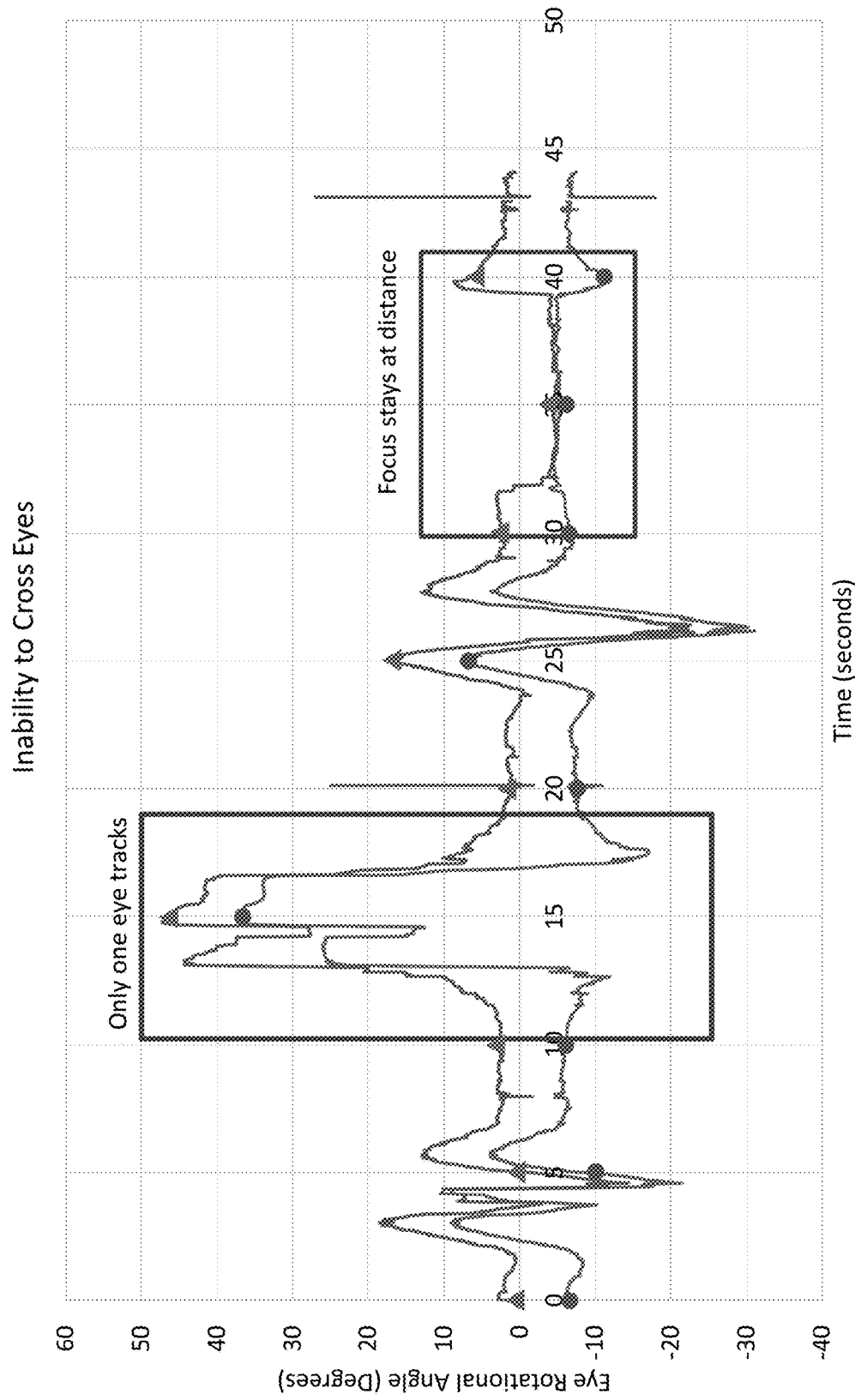
FIG. 16 is an illustration of an exemplary chart which may be output by the system of the present disclosure and which shows the results of a Lack of Convergence Test for tracking eye movement where the test subject is likely impaired.

In contrast to the chart illustrated in FIG. 15, the chart in FIG. 16 illustrates a failure of the Lack of Convergence Test where the test subject is unable to cross his or her eyes. That is, FIG. 16 illustrates results which would be expected from a test subject in an impaired state.

Figure 17:
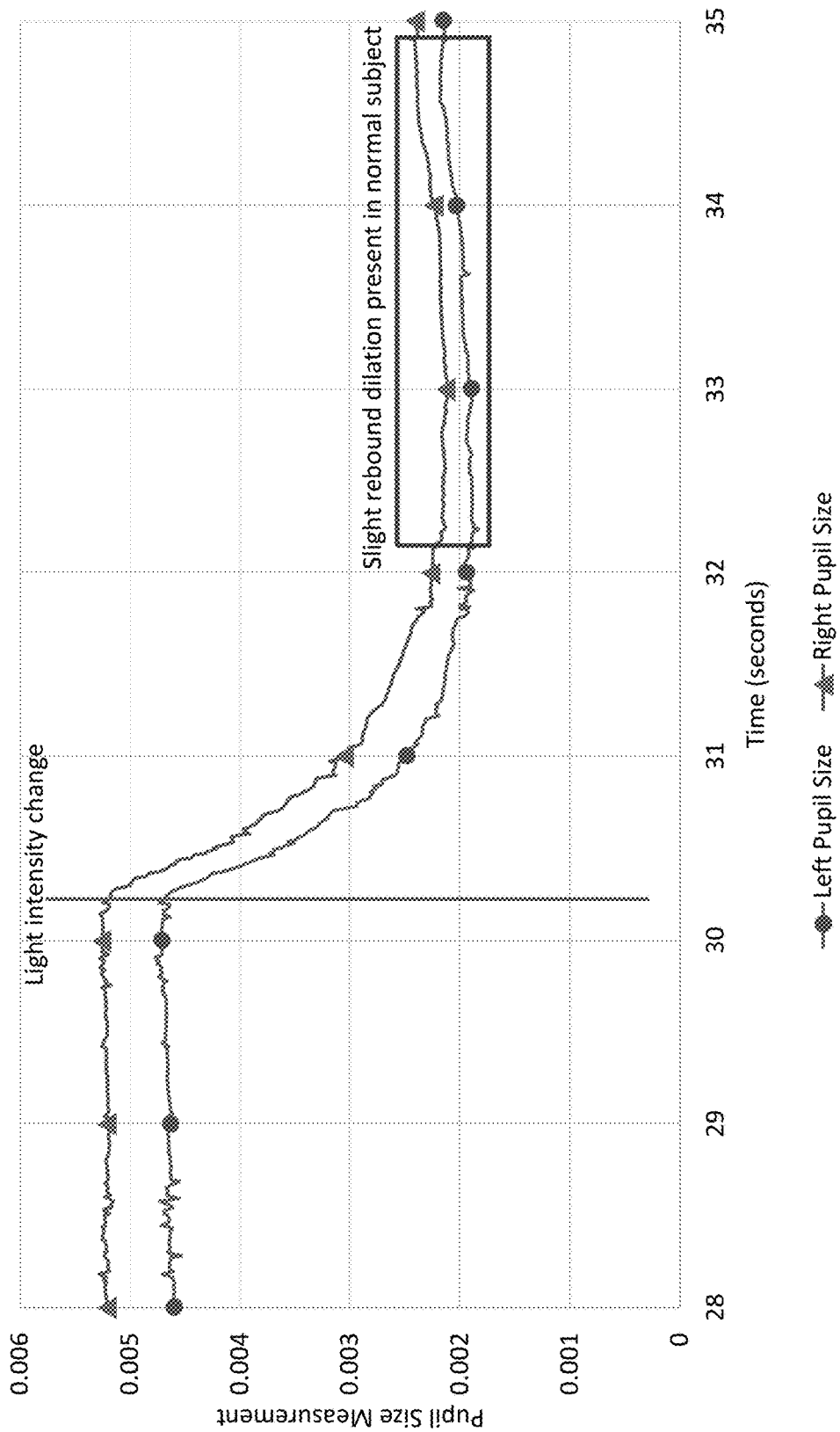
FIG. 17 is an illustration of an additional exemplary chart which may be output by the system of the present disclosure and which shows the results of a Pupil Size Test where the test subject is likely not impaired.

Finally, in FIG. 17, a chart titled "Pupil Size Test" is provided which shows exemplary eye tracking results when the test subject's pupil's decrease in size in response to a change in scene brightness. The Pupil Size result in the chart of FIG. 17 is further representative of the type of information output as part of the impairment indication information 140 described above. More particularly, FIG. 17 includes values that would be expected for the scene settings 176, left pupil size 178, and right pupil size 180 testing parameters, as indicated by the Y-axis labeled "Pupil Size Measurement". Such data would be generated and collected over the timestamp testing parameter values shown on the X-axis and during administration of the Pupil Size Test as described above. Moreover, the testing parameter values, as represented by the data plot lines for the pupil of each eye in FIG. 17, are representative of values which may indicate non-impairment. This is because the left and right pupil sizes decreased nearly immediately concurrent with the light intensity change indicated in the chart shortly after the 30 second timestamp on the X-axis. Moreover, a slight rebound in pupil size is indicated between the 32 and 35 second timestamps, which is representative of pupil dilation for test subjects in a non-impaired state.

EXAMPLES

Various impairment tests were performed using a VR headset 102 according to the embodiments described above. That is, a VR headset 102 configured for detecting impairment of a test subject, as discussed above, was used at a Drug Recognition Expert ("DRE") training event at the Ohio State Highway Patrol Training Academy. The DRE training event was an alcohol "wet lab", where controlled doses of alcohol were administered to volunteer test subjects. These wet labs are useful to train DRE students and officers in conducting field sobriety testing on volunteer test subjects. Wet labs like these are also useful for testing new impairment detecting devices, such as the VR headset 102 described herein.

During the lab, volunteer test subjects were asked to wear a VR headset 102 configured to act as an impairment sensor. Data was then gathered from sober and impaired subjects. Each subject that used the VR headset 102 was tracked with a unique ID number along with their most recent blood alcohol content (BAC) reading as measured by the officers conducting the lab. In total, eight (8) test subjects volunteered to use the VR headset 102 along with seven (7) other sober individuals. Most test subjects that used the VR headset 102 provided a sober baseline measurement before consuming alcohol. In addition, one or more additional tests were then performed at varying BAC levels to obtain measurements of impairment. All the relevant eye and testing data was recorded by sensor software of the VR headset 102 during each test.

The VR headset 102 conducted five (5) tests on each test subject. During each test, the VR headset 102 tracked both the test subject's eyes and gaze relative to an object. These five tests included: (1) a smooth tracking test; (2) a horizontal gaze nystagmus (HGN) test; (3) a vertical gaze nystagmus (VGN) test; (4) a lack of convergence (LOC) test; and, (5) a pupil response test. According to the DRE training material, alcohol affects the test subject's performance on each of these five tests. However, altered performance was not exhibited by all test subjects on these tests, depending on each test subject's level of alcohol intoxication, and some users exhibited characteristics of impairment despite being sober.

A general look at the data obtained from these tests reveals that LOC test failures are easily discernable (FIGS. 23-26). Moreover, numerical metrics that accurately assess whether the test subject was able to cross their eyes can be readily developed from the LOC test. The smooth tracking tests (FIGS. 18-19) also show a clear line between impaired and sober subjects, but a more advanced algorithm is utilized for the software to assess the "smoothness" of the tracking compared with the LOC test. The HGN and VGN tests (FIGS. 20-22) revealed gaze nystagmus in some test cases with impaired subjects, but not all. This could be due to many factors, but may be at least partially attributed to the limited field of view of the headset 102 preventing the software from pushing the eyes to an extreme enough angle for nystagmus to be present.

Figure 27:
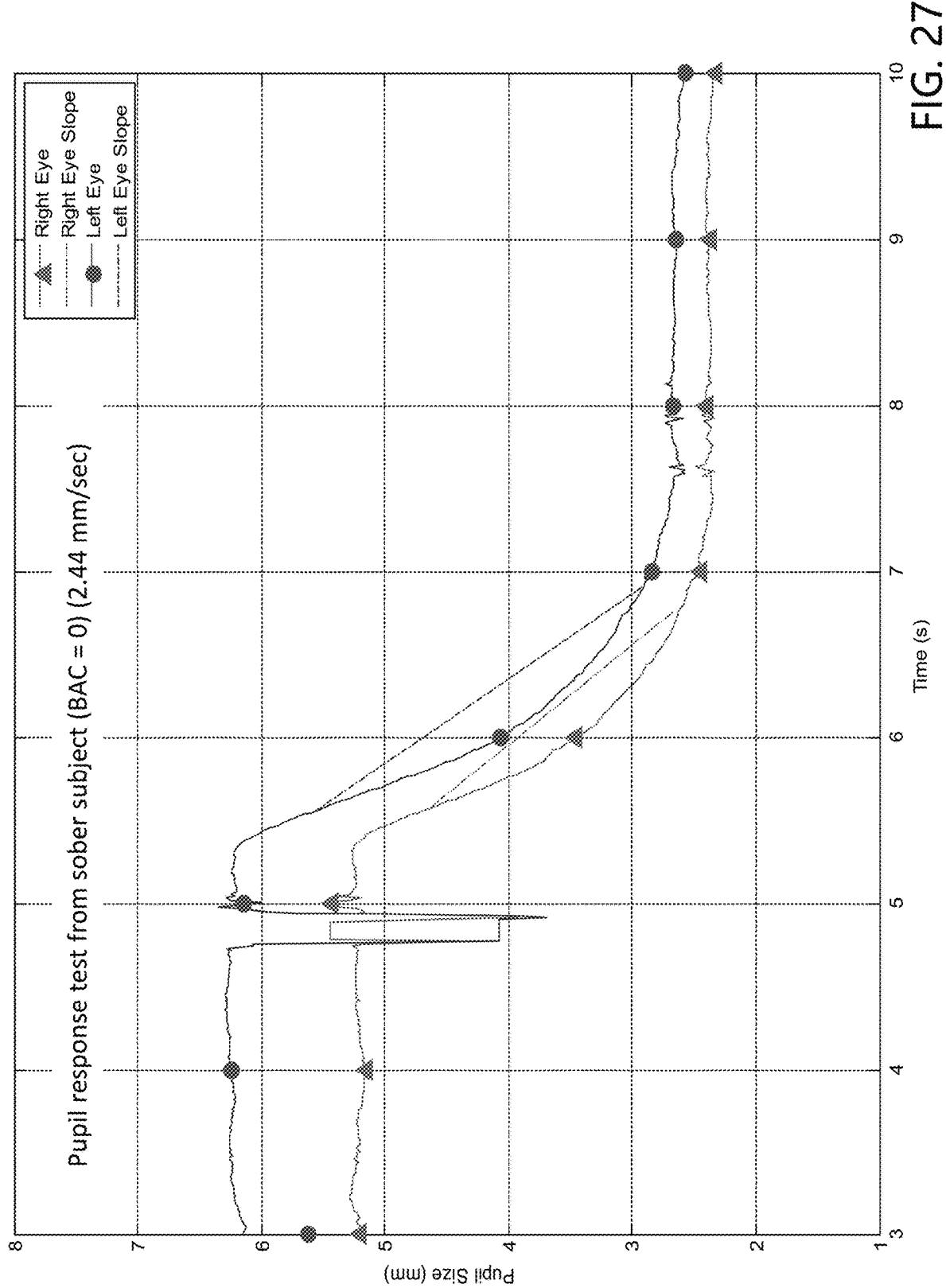
FIG. 27 is a chart output by the system of the present disclosure and which shows the results of a pupil response test where the test subject is sober; and, FIG. 28 is a chart output by the system of the present disclosure and which shows the results of a pupil response test where the test subject is intoxicated.

The pupil response tests (FIGS. 27-28) yielded very precise results for almost all test subjects. The pupil size for each test subject in high and low light conditions was easily extracted. A precise rate of change for each pupil when the lighting was changed from darkness to light was also able to be extracted. However, there was not a clear correlation between pupil response rate and intoxication level, as some subjects experienced a slower response rate after consuming alcohol, but others experienced an increased response rate.

Overall, based on a review of the data gathered at the aforementioned wet lab, the VR headset 102 successfully and accurately implemented visual tracking tests that were able to adequately detect physical evidence of impairment. The physical evidence of impairment detected by the VR headset 102 is the same as the impairment indicators exposed in known sobriety tests which generally must be performed manually by DRE officers.

Though these tests were conducted on subjects dosed with alcohol, the aforementioned wet lab still provides useful information to the VR headset's 102 applicability in the detection of other forms of impairment, such as *cannabis* impairment. The HGN and VGN tests (FIGS. 20-22) that are more difficult to detect and that weren't as present in the subjects at this event are not known to be good indicators of *cannabis* impairment. Lack of convergence, dilated pupils, and a transient effect called rebound dilation that occurs in the pupil response test are the reliable signs of *cannabis* impairment. The data gathered by the VR headset impairment sensor for both the LOC test and the pupil response tests revealed that impairment symptoms were very apparent in the data.

Example 1—Smooth Tracking Test

Figure 18:
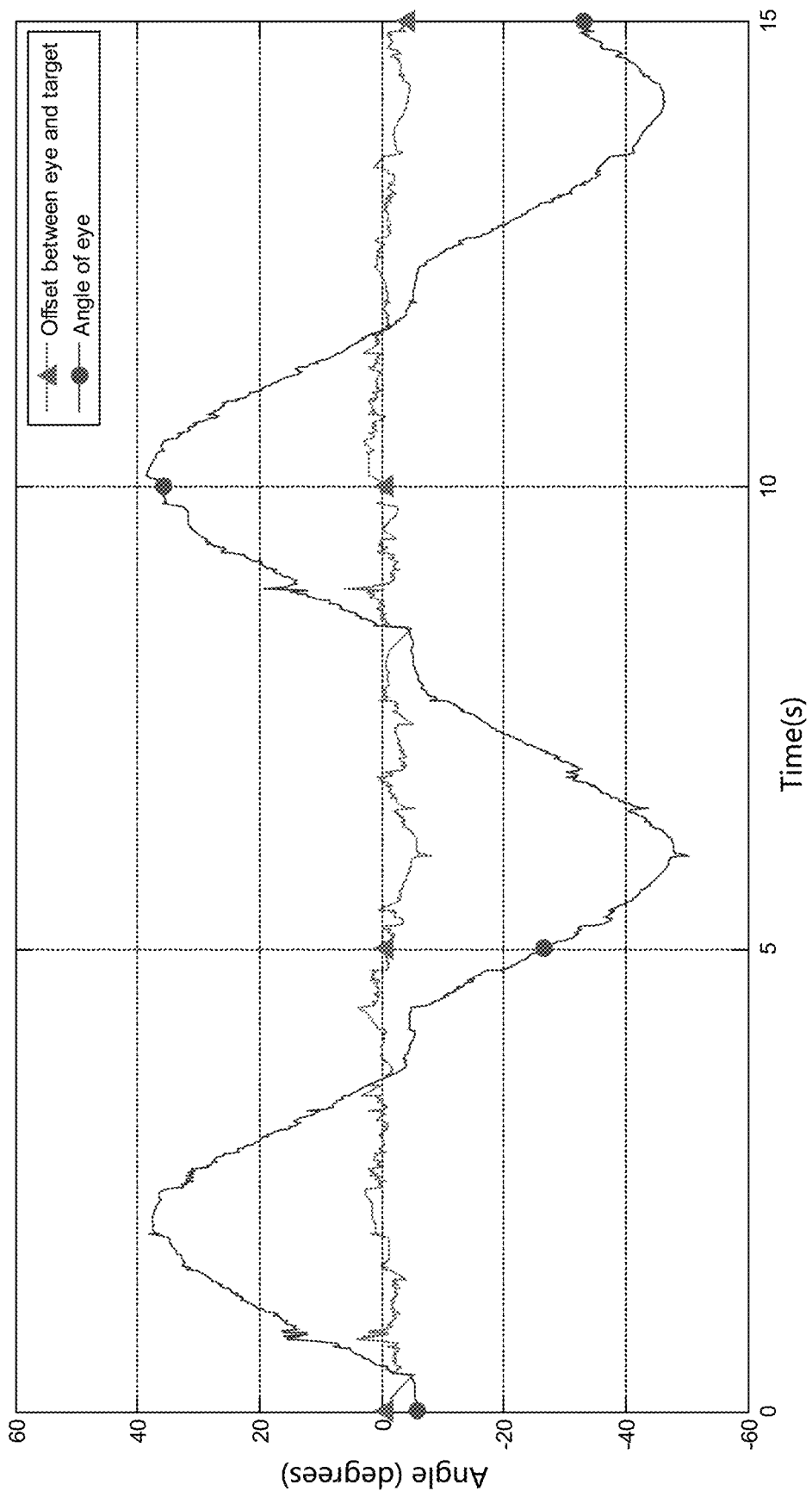
FIG. 18 is a chart output by the system of the present disclosure and which shows the results of a smooth tracking test where the test subject is sober.
Figure 19:
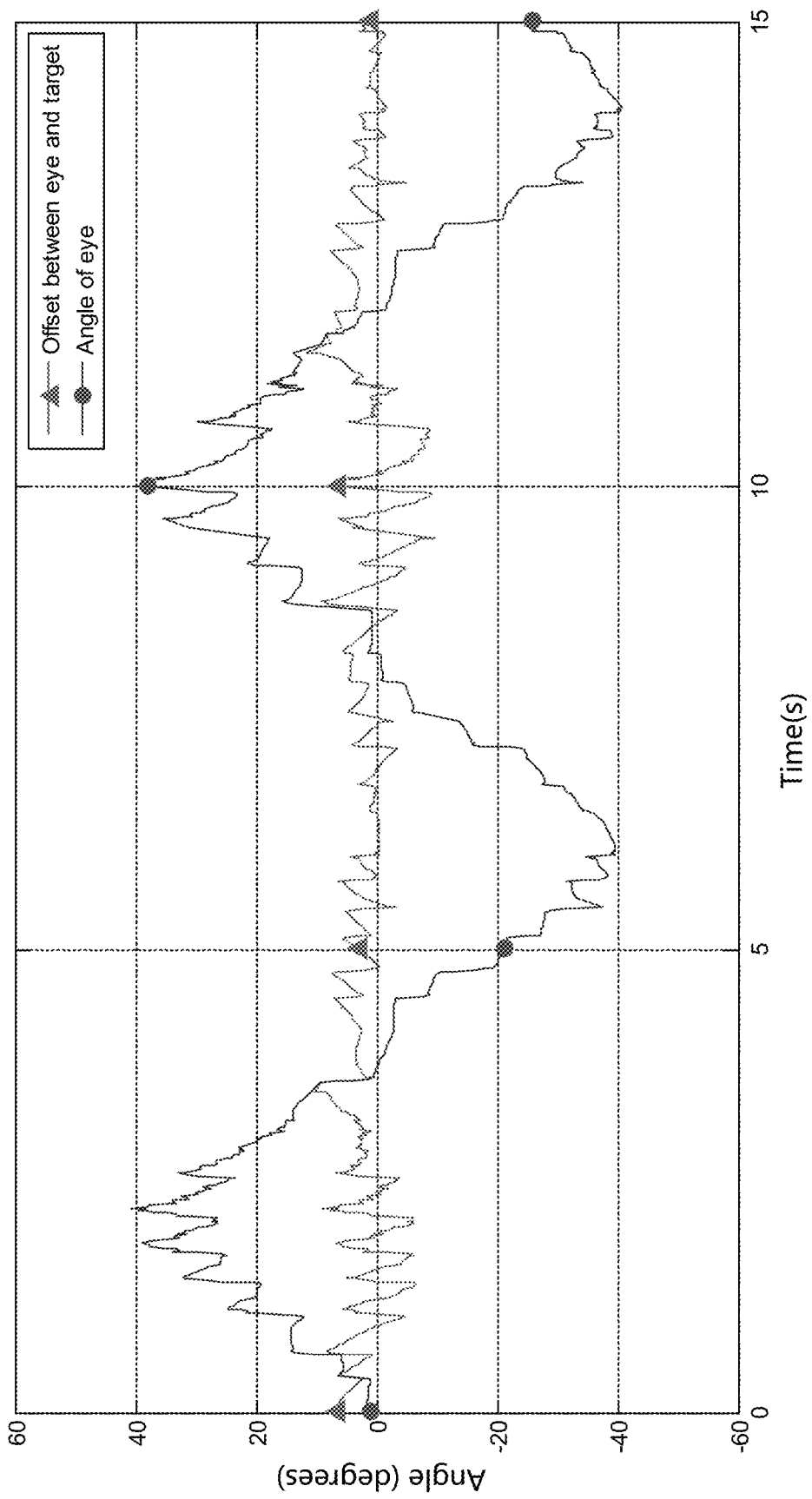
FIG. 19 is a chart output by the system of the present disclosure and which shows the results of a smooth tracking test where the test subject is intoxicated.

The smooth tracking test measured the test subject's ability to track an object that moves horizontally back and forth in front of them. A sober subject can move their eyes smoothly along with the object as it moves, but an impaired subject will exhibit jumpy, jittery, or delayed tracking. FIG. 18 shows an example of a sober subject in the tracking test. When the subject becomes impaired, their inability to smoothly track the object is easily visible in the test data. FIG. 19 shows an example of an intoxicated subject in this test. The jerky tracking shown in FIG. 19 is easy to distinguish visually and is easily detected by the software of the VR headset 102.

Example 2—HGN and VGN Tests

Figure 20:
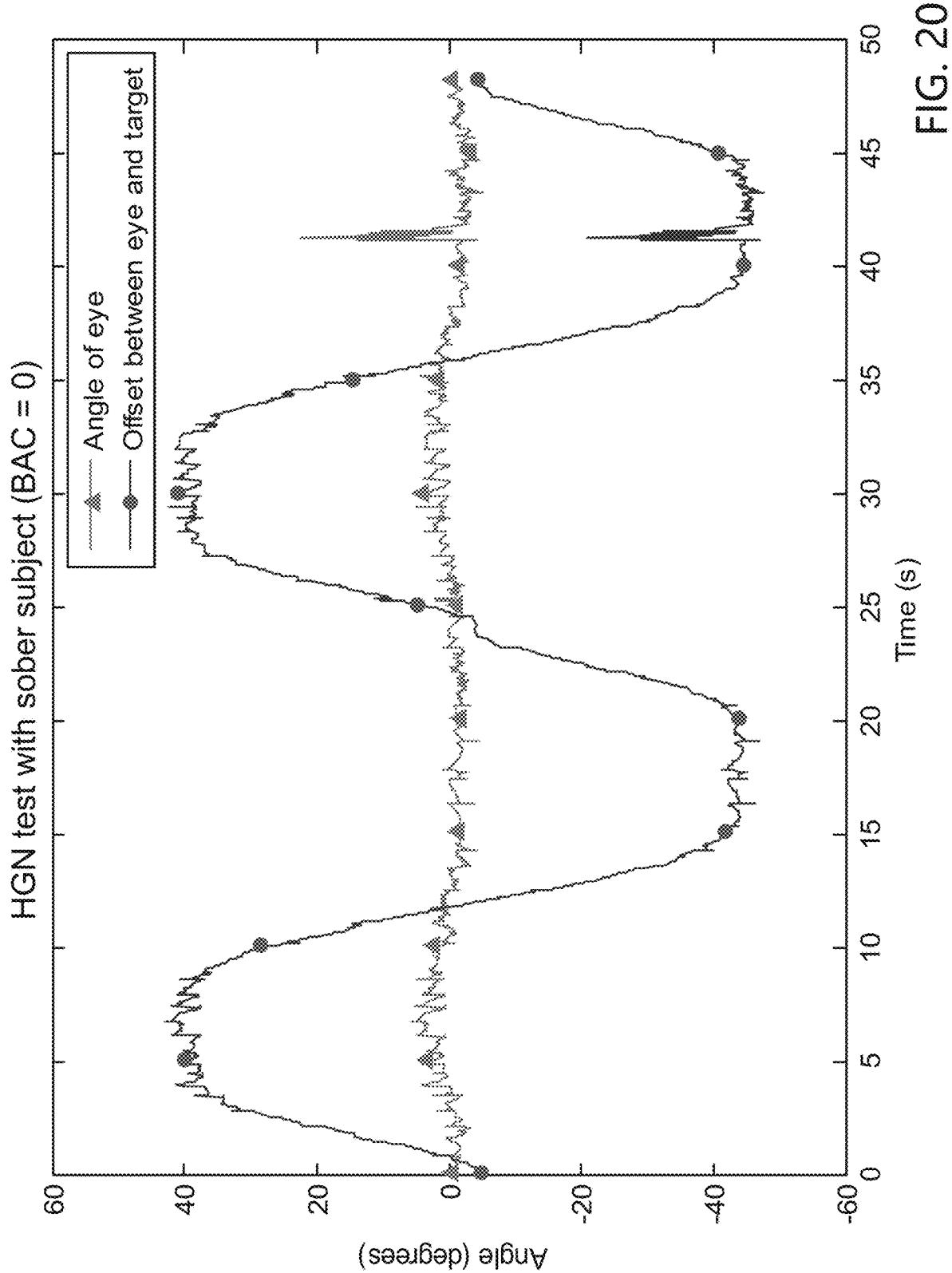
FIG. 20 is a chart output by the system of the present disclosure and which shows the results of a gaze nystagmus test where the test subject is sober.
Figure 21:
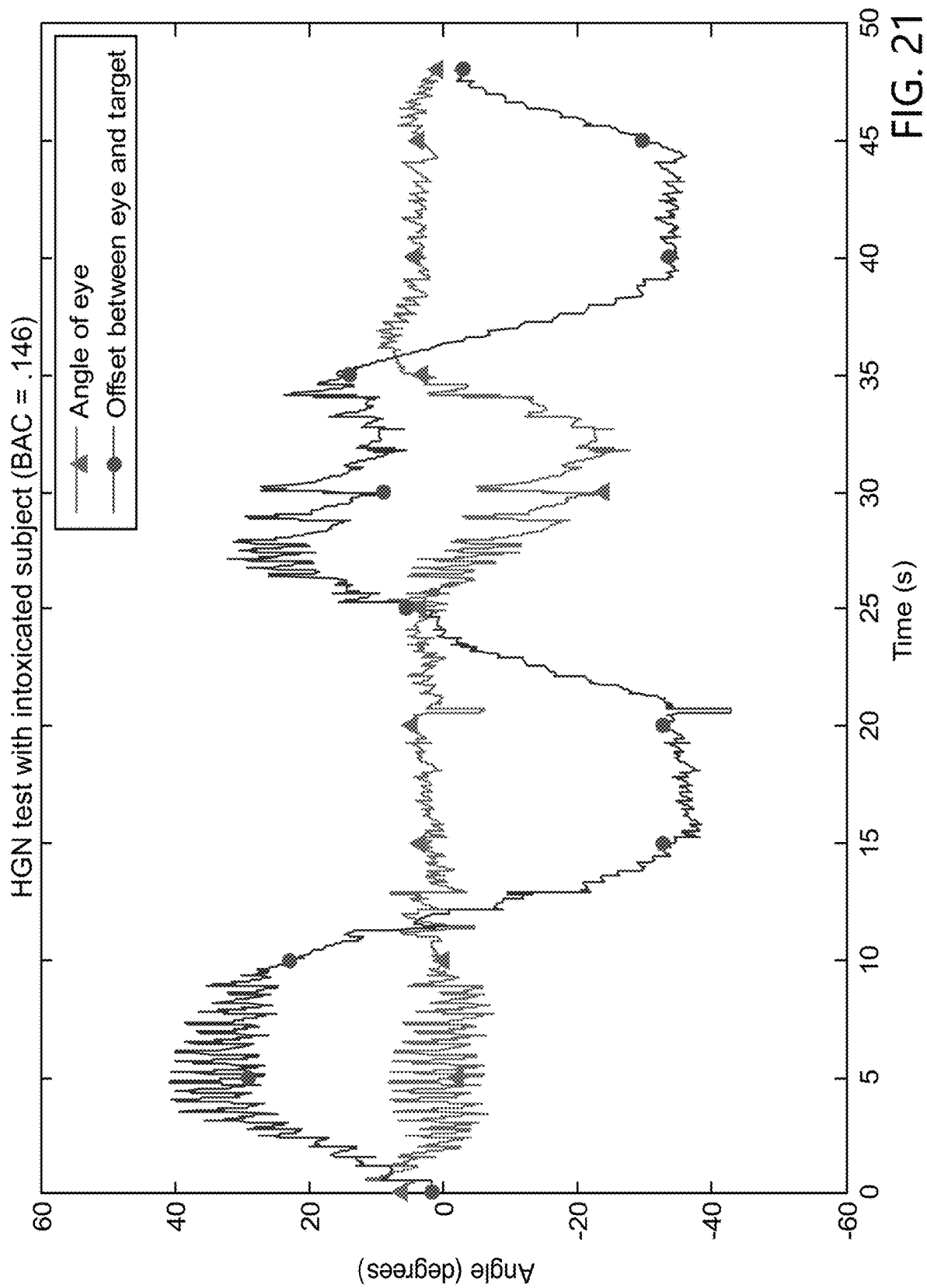
FIG. 21 is a chart output by the system of the present disclosure and which shows the results of a gaze nystagmus test where the test subject is intoxicated.

The horizontal and vertical gaze nystagmus tests moved the tracked object to the edge of the test subject's vision to induct nystagmus or jitter in the subject's eyes. According to the DRE instructors, horizontal nystagmus is more common and tends to be present at a lower level of intoxication than vertical nystagmus. Both forms of nystagmus also tend to present themselves at smaller eye offset angles as the test subject becomes more intoxicated. Not all users exhibited nystagmus at the angles of the tracking object created by the VR headset 102, but there were clear examples of nystagmus in more intoxicated subjects. FIGS. 20 and 21 show a test subject's baseline and intoxicated HGN tests, respectively.

Figure 22:
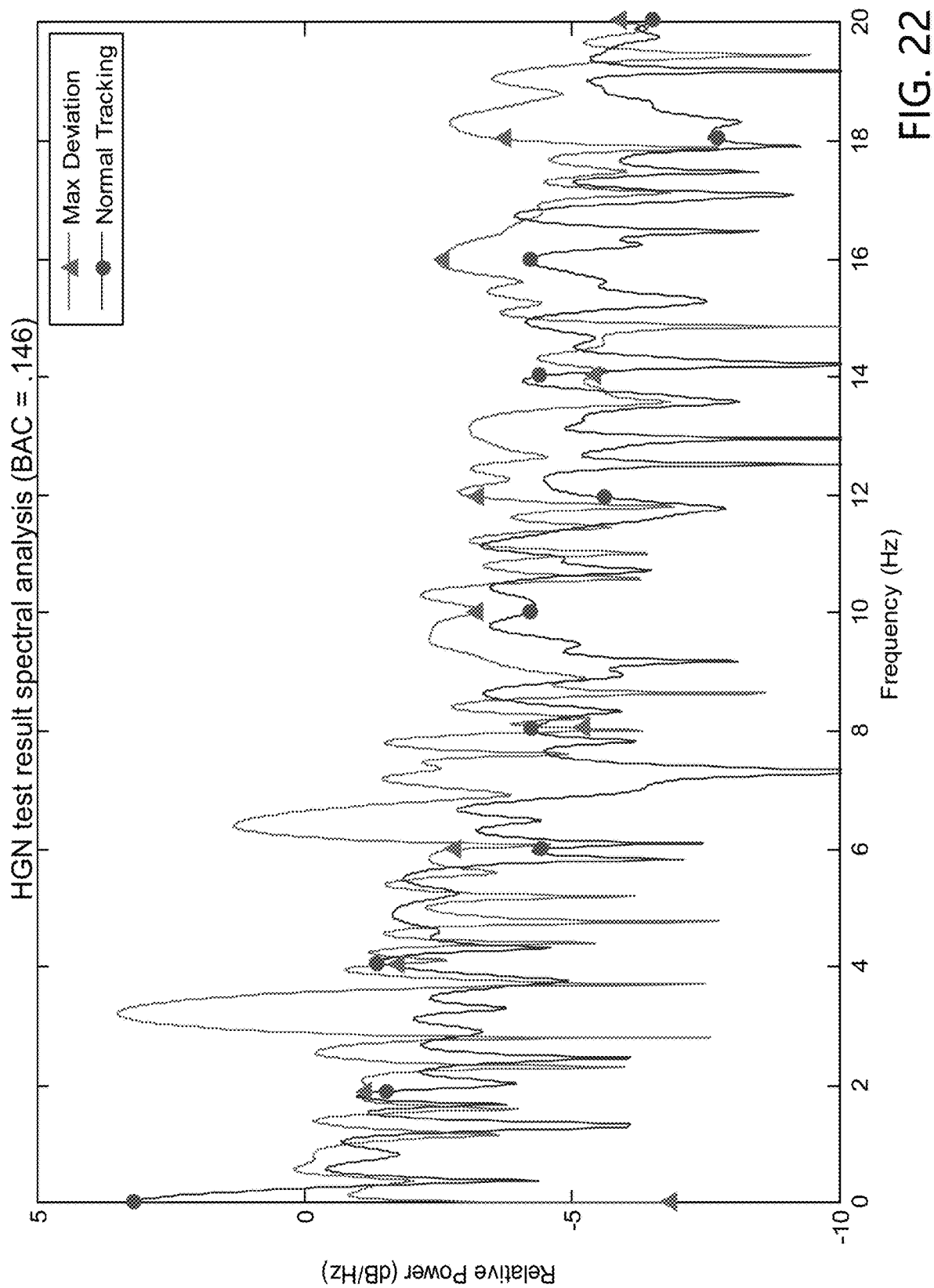
FIG. 22 is a chart output by the system of the present disclosure and which shows the results of a gaze nystagmus test where the test subject is intoxicated, and which includes a spectral analysis.

Conducting HGN and VGN tests in software also permitted the analysis of nystagmus in ways that an officer would not be able to in the field. For example, FIG. 22 shows a spectral analysis of the test result from FIG. 21 that shows very clear jitter at about 3.5 Hz. Spectral analysis like that in FIG. 22 is useful both for identifying the presence of nystagmus but also for categorizing different types of nystagmus based on the frequency of the jitter. This categorizing of different types of nystagmus cannot by performed by an officer in real time during a field test.

Example 3—LOC Test

Figure 23:
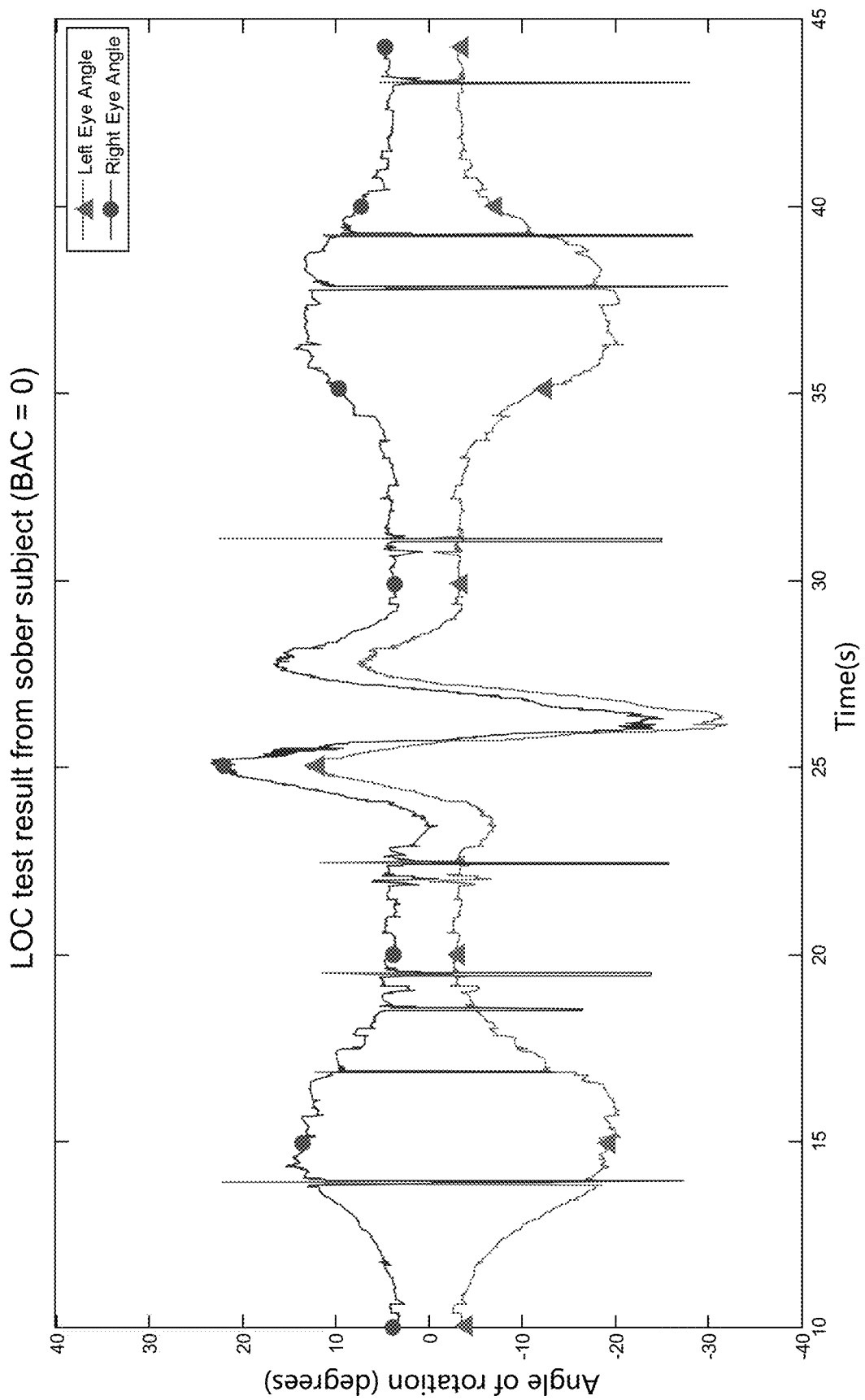
FIG. 23 is a chart output by the system of the present disclosure and which shows the results of a lack of convergence test where the test subject is sober.
Figure 24:
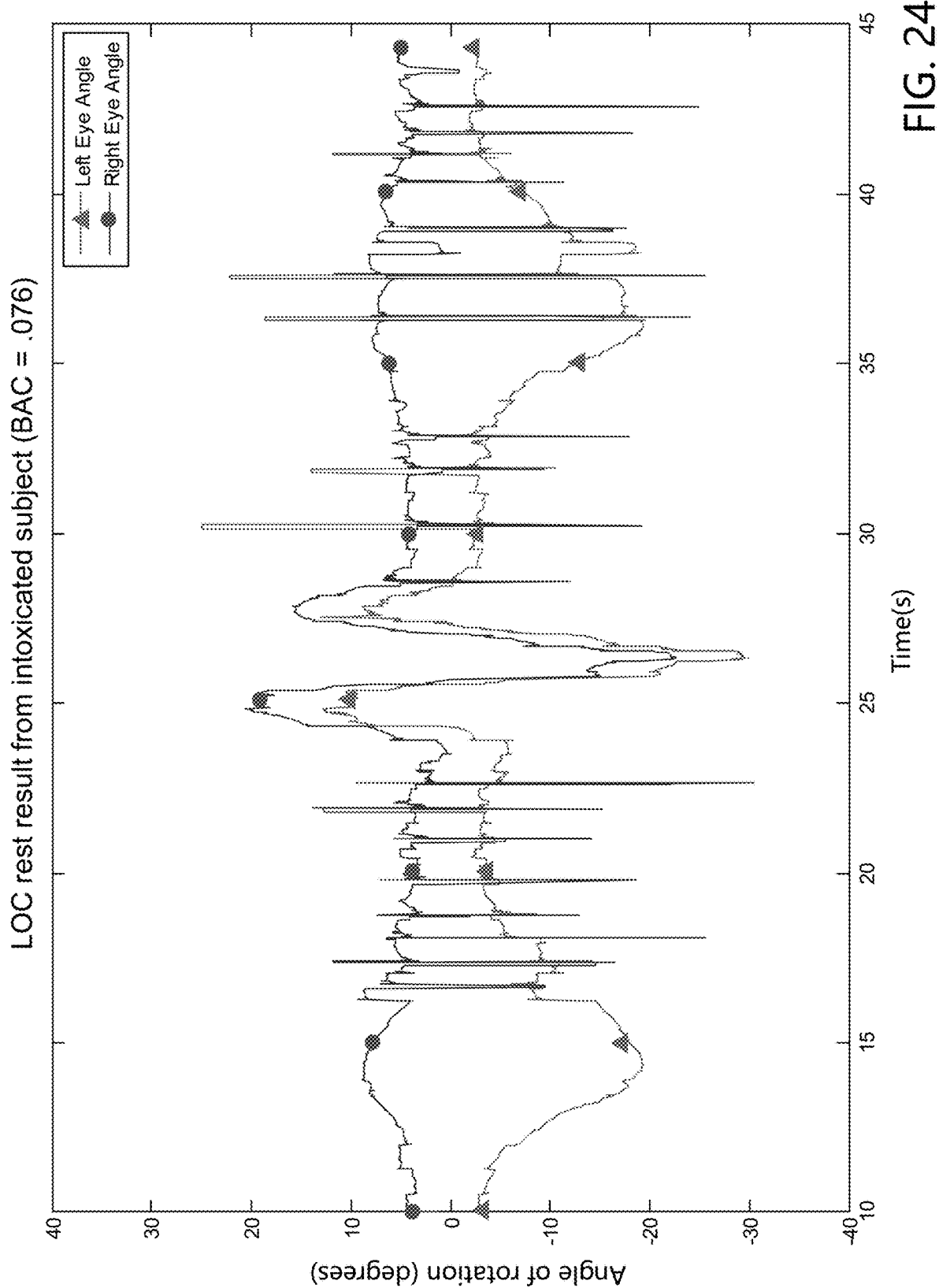
FIG. 24 is a chart output by the system of the present disclosure and which shows the results of a lack of convergence test where the test subject is intoxicated.

The LOC test involved moving the tracked object towards the bridge of the test subject's nose and assessing the test subject's ability to cross their eyes and maintain focus on the tracked object. The angles of the subject's eyes were measured by the sensor directly, so the data from this test clearly shows the ability or inability of a test subject to cross their eyes. The DRE training material indicates that alcohol contributes to a test subject exhibiting lack of convergence. FIG. 23 shows an average quality sober result of the LOC test. The test subject from the FIG. 23 was able to cross their left eye more accurately than their right eye but could still reach a reasonable level of convergence. As the test subject becomes impaired, lack of convergence can be demonstrated in various ways. With the test subject from FIG. 23, intoxication reduced the ability of the right eye to converge on the tracking object. This result is shown in FIG. 24.

Figure 25:
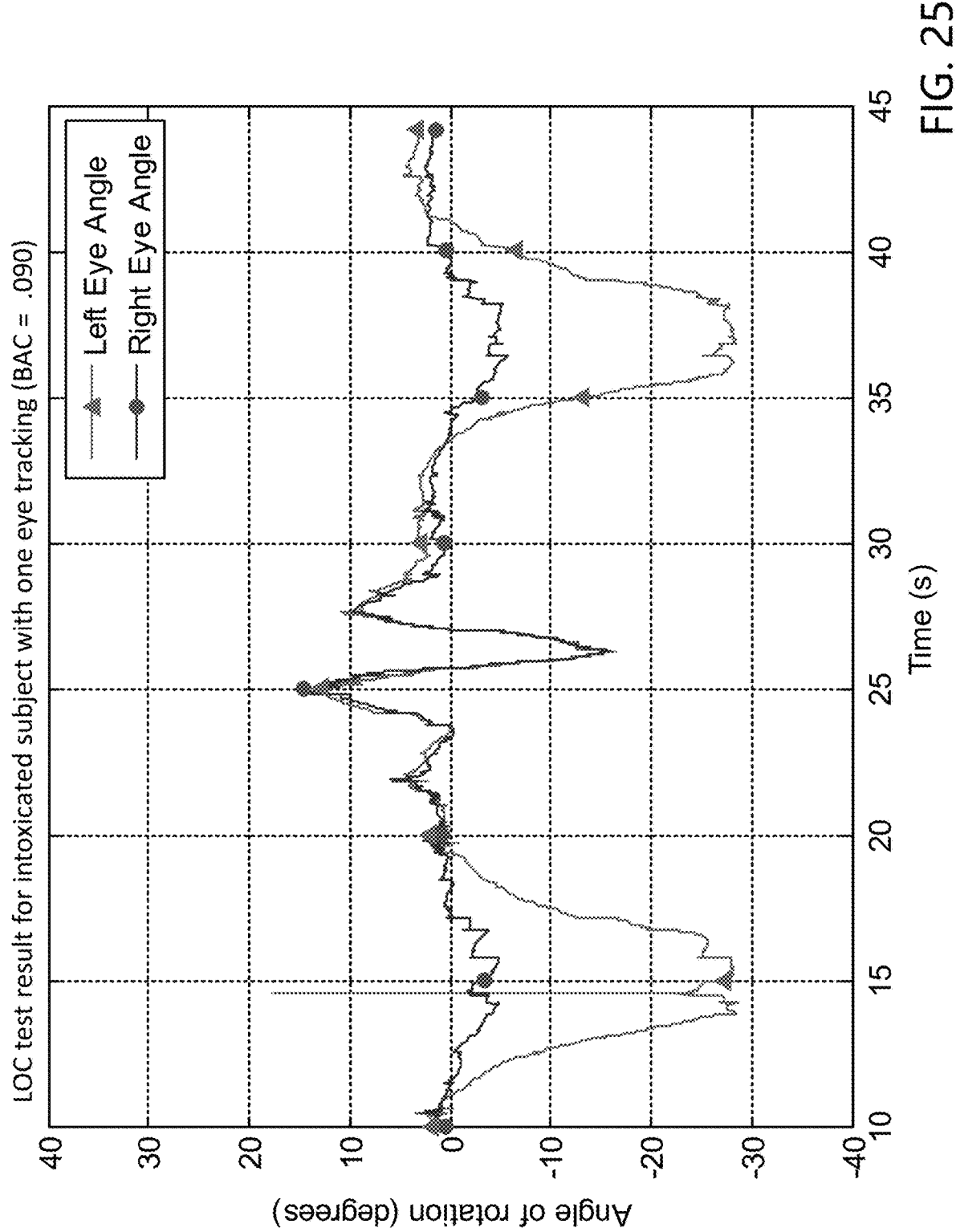
FIG. 25 is a chart output by the system of the present disclosure and which shows the results of a lack of convergence test with one eye tracking where the test subject is intoxicated.
Figure 26:
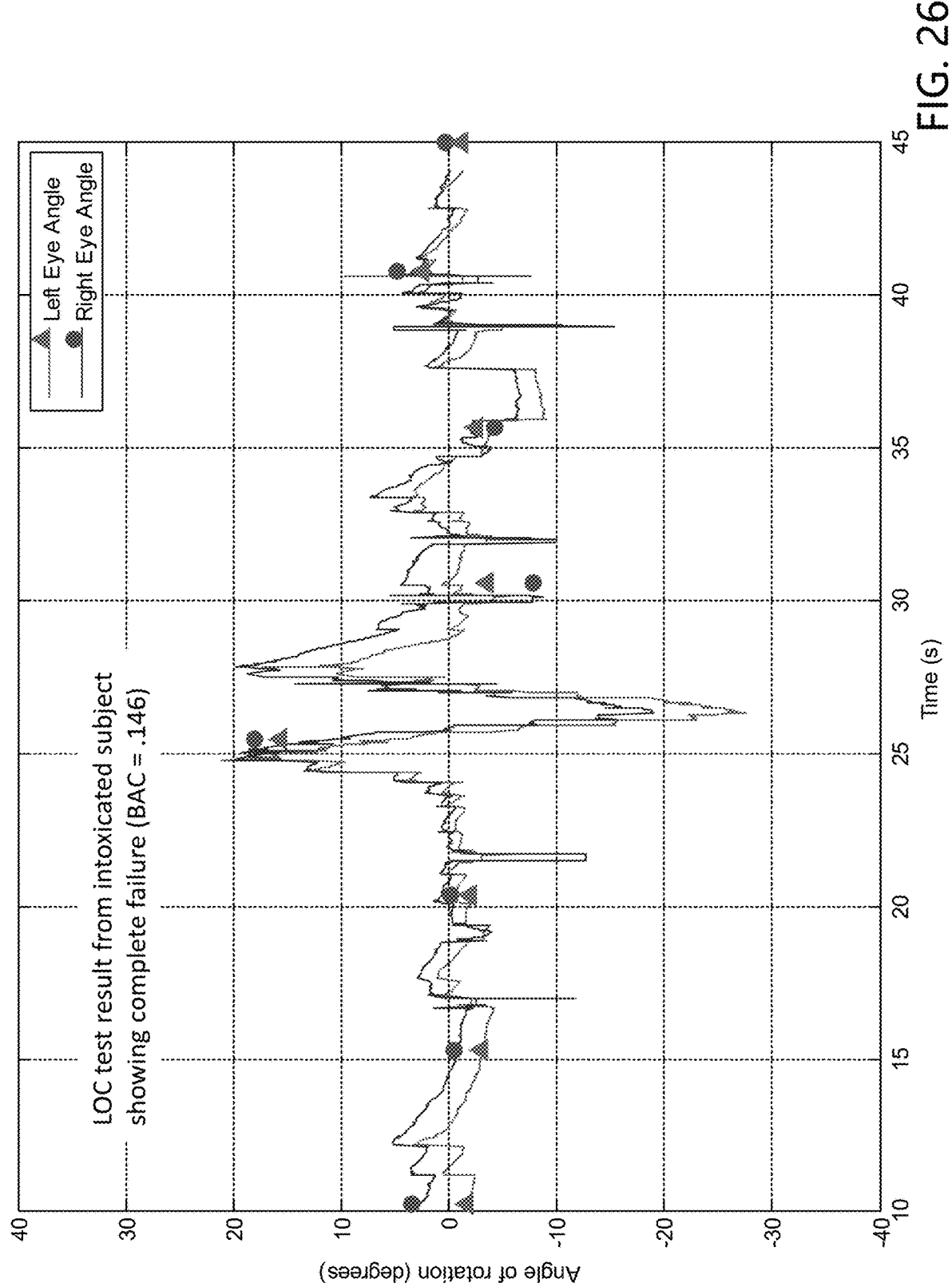
FIG. 26 is a chart output by the system of the present disclosure and which shows the results of a lack of convergence test where the test subject is intoxicated and a complete failure to converge is observed.

The LOC test above shows a subtler example of lack of convergence, where both eyes moved towards the stimulus but were not able to accurately converge. Some test subjects exhibited a more pronounced lack of convergence, such as the test subjects shown in FIGS. 25 and 26. In FIG. 25, one eye of the test subject tracked correctly, and the other eye went the wrong direction. In FIG. 26, the test subject was completely unable to track the object as it moved toward the test subject.

Example 4—Pupil Response Test

The pupil response test measured the test subject's reaction to light by examining how the pupils responded to changing light intensities. This was conducted by putting the test subject in a low light condition for 90 seconds then quickly shining a bright light into the eyes, thereby causing the test subject's pupils to restrict. The test examines the resting pupil size in both the low light and bright light conditions, as well as the rate of change of the pupil size when exposed to light. The DRE training material suggests that test subjects under the influence of alcohol should have normal pupil sizes in any given lighting condition but have a slowed reaction speed to light.

The pupil size measurements from the VR headset 102 during testing was accurate and repeatable. Both the change in steady state pupil size and the transient size change were easily visible, as seen in the baseline test shown in FIG. 27 and the impaired test shown in FIG. 28. Some noise resulted in the measurements from test subjects with particularly droopy eyelids and subjects that blinked frequently. However, as seen at about the 5 second mark in FIG. 27, the VR headset 102 registers this as extremely high amplitude noise that is easily filtered out of the data. Test subjects tended to blink more and create more noise in the data as intoxication levels increased. However, software data analysis was still able to extract the correct response rate slope, as shown in FIG. 28.

Figure 28:
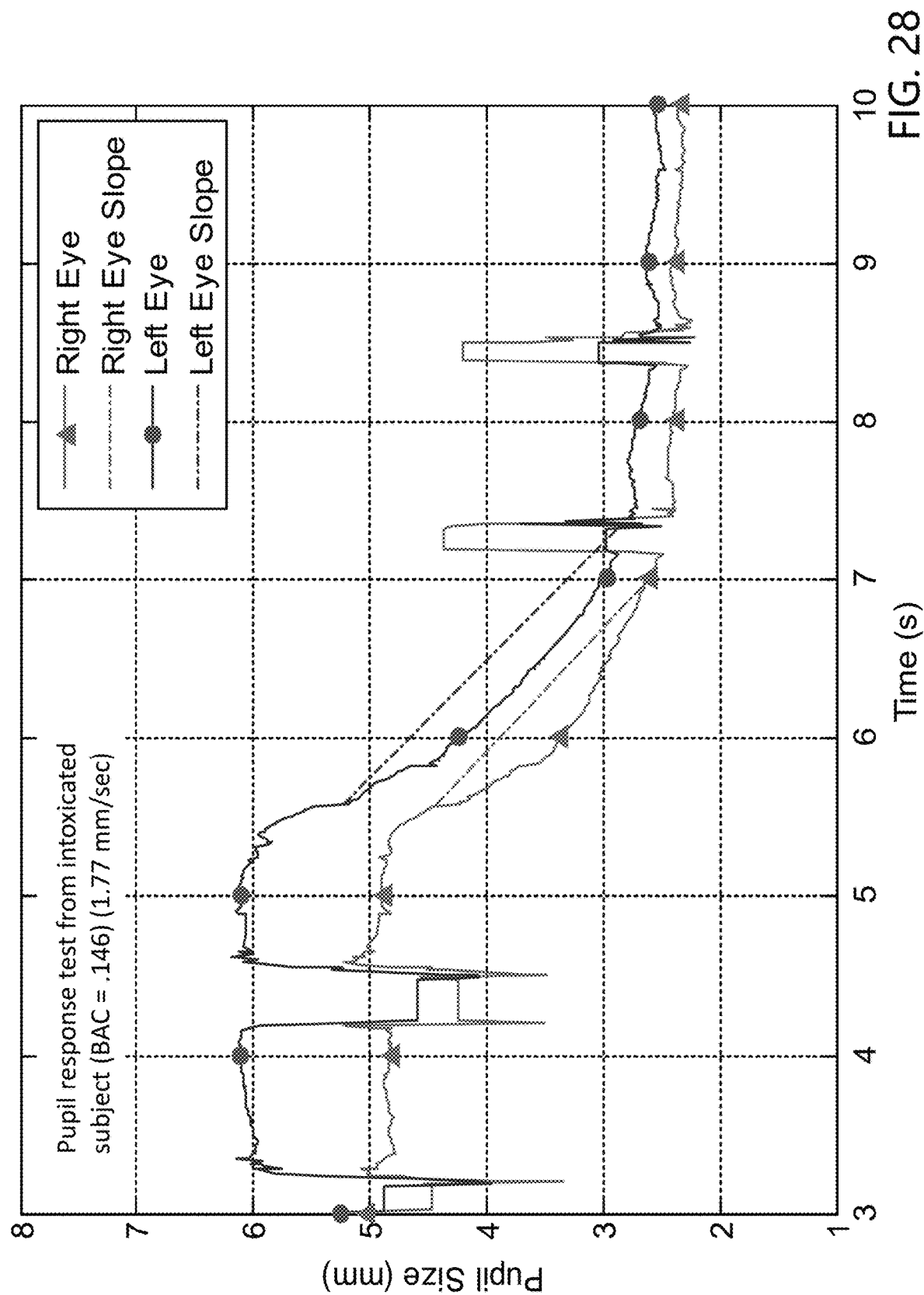

While the subject of FIG. 28 exhibited about a 25% reduction in pupil reaction time, the pupil reaction time in other subjects sped up after being dosed with alcohol. Additionally, some subjects that had pupil reaction times slow after consuming alcohol still had reaction times faster than sober baselines of other subjects. A larger sample size and more refined data analysis techniques may be able to more successfully use pupil response rate to assess intoxication levels.

Regardless of the aforementioned inconsistencies, the VR headset 102 was able to accurately and consistently measure both pupil size and transient response rates for almost all tests. Even a crude slope detection algorithm was able to successfully detect the pupil size rate of change in most cases without prefiltering the blinks from the data, which gives confidence that a more developed analysis approach would be extremely consistent.

CONCLUSIONS

Data from the examples discussed above clearly showed the physical symptoms of impairment that officers look for in each of the 5 currently implemented impairment tests. The consistency, sensitivity, usability, and reliability of the VR headset 102 will be improved with larger sample sizes, but the preceding examples show that the impairment "clues" which officers look for are detectable by the VR headset 102 in at least some subjects at relatively low levels of impairment.

The system 100 including the VR headset unit 102 disclosed herein may be implemented with the capability to check that the device measurements are within allowed tolerances. These measurements may include but are not limited to eye angle, pupil diameter, head position/angle, and measurement frequency. In this regard, the VR headset unit 102 may be equipped with an optional calibration check instrument (not shown). Such a calibration check instrument generally includes a fixture with one or more mannequin style heads or partial heads including sets of false eyes or other representations that simulate eyes. The fixture is configured to provide various pupil diameters and eye angles to check the accuracy of the device under test. The fixture of the calibration check instrument may also include the capability to check the accuracy of head position and head angle measurements, in addition to checking measurement frequency to ensure accuracy of tests that involve time components. In some embodiments, the fixture may be mechanical. In other embodiments, the fixture may be driven by electric motors. Moreover, the false eyes may be fixed in position or they may be dynamic. The head position and angle may also be fixed or dynamic. Finally, the fixture may include of one or more sets of heads, each with one or more sets of false eyes.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

To aid the Patent Office and any readers of this application and any resulting patent in interpreting the claims appended hereto, applicants do not intend any of the appended claims or claim elements to invoke 35 U.S.C. § 112(f) unless the words "means for" or "step for" are explicitly used in the particular claim.

The invention claimed is:

1. A system configured to implement one or more tests indicative of impairment due to drugs or alcohol, the system comprising:
   a VR headset configured to display at least one virtual environment and at least one virtual object in the environment;
   an eye tracking component; and
   a processor in communication with a memory comprising instructions to measure a change in one or more features of a test subject's eyes with the eye tracking component,
   wherein the change in one or more features of the test subject's eyes is induced by a manipulation of the at least one virtual environment or the at least one virtual object displayed by the VR headset, and wherein the memory further comprises a comparison component having instructions to output drug classification identification results with a probability or percent match associated with at least one drug class.

2. The system of claim 1, further comprising one or more sensors in communication with the eye tracking component, the one or more sensors including cameras, body tracking sensors, accelerometers G-sensors, gyroscopes, proximity sensors, electrodes for obtaining EEG data, or thermometers and other temperature sensors or non-invasive sensing devices.

3. The system of claim 1, further comprising a light blocking device mounted to the VR headset.

4. The system of claim 1, further comprising one or more light sources mounted to the VR headset.

5. The system of claim 1, wherein the memory further comprises a testing component having instructions to perform the one or more tests indicative of impairment, wherein the testing component outputs parameter values for each of the one or more tests.

6. The system of claim 5, wherein the comparison component further comprises instructions to correlate the parameter values output by the testing component with parameter values associated with predetermined baseline standards of impairment.

7. The system of claim 6, wherein the predetermined baseline standards of impairment include parameter values related to one or more of a timestamp, a test state, scene settings, left pupil size, right pupil size, eye gaze to target cast distance, eye gaze to target cast vertical angle, eye gaze to target cast horizontal angle, eye horizontal angle to normal, eye vertical angle to normal, distance between eye focus points, eye position, and eye jitter.

8. The system of claim 6, wherein the memory further comprises a decision component having instructions to determine a level of impairment based on the correlation of the comparison component.

9. The system of claim 8, wherein the memory further comprises an output component to output the impairment prediction of the decision component or the correlation of parameter values of the comparison component.

10. The system of claim 1, further comprising a host computer associated with the VR headset and a display device for the host computer, wherein the display device is configured to show a real-time representation of the test subject's eyes.

11. The system of claim 10, wherein the real-time representation includes a pair of animated eyes and a visual depiction of tracking by the eye tracking component.

12. The system of claim 1, further comprising one or more peripheral devices connected in communication with the VR headset and configured to supplement data generated by the eye tracking component.

13. The system of claim 1, wherein the manipulation of the at least one virtual environment includes a change in brightness, contrast, or color of a scene in the virtual environment.

14. The system of claim 1, wherein the manipulation of the at least one virtual object includes a change in brightness, contrast, color, direction, or location of the virtual object.

15. The system of claim 1, wherein the manipulation of the at least one virtual object includes random movement, discrete increasing angular movement, smooth movement, or jittery movement of the virtual object.

16. A method of indicating impairment due to drugs or alcohol, the method comprising:

displaying at least one virtual environment and at least one virtual object in the environment with a VR headset, wherein the VR headset includes an eye tracking component and a processor in communication with a memory, the memory including instructions for measuring a change in one or more features of a test subject's eyes with the eye tracking component;

manipulating the at least one virtual environment or the at least one virtual object displayed by the VR headset;

measuring parameter values representative of the change in one or more features of the test subject's eyes after manipulating the virtual environment or the virtual object; and correlating the measured parameter values with predetermined baseline standards of impairment; and, predicting a level of impairment based on the correlation with the predetermined baseline standards of impairment and outputting the prediction;

determining drug classification identification results with a probability or percent match associated with at least one drug class; and, outputting the correlation with the predetermined baseline standards of impairment.

17. The method of claim 16, wherein measuring parameter values further comprises recording at least one of a timestamp, a test state, scene settings, left pupil size, right pupil size, eye gaze to target cast distance, eye gaze to target cast vertical angle, eye gaze to target cast horizontal angle, eye horizontal angle to normal, eye vertical angle to normal, distance between eye focus points, eye position, and eye jitter.

18. The method of claim 16, wherein manipulating the at least one virtual object comprises changing a brightness, contrast, color, direction, location, or movement of the virtual object.

19. The method of claim 16, wherein manipulating the at least one virtual environment comprises changing a brightness, contrast, or color of a scene in the virtual environment.

20. A method of operating a VR headset to indicate a level of impairment due to drugs or alcohol, the method comprising: initiating one or more software components configured to perform one or more tests with the VR headset which indicate impairment due to drugs or alcohol; running the selected test according to instructions provided by the one or more software components; activating an eye tracking hardware component to begin recording raw eye tracking data and conditions of at least one virtual tracking object and at least one virtual environment generated by the VR headset; and saving and outputting data generated after running the selected test, and wherein the data outputted after running the selected test includes drug classification identification results with a probability or percent match associated with at least one drug class.

* * * * *